(12) United States Patent
Adam

(10) Patent No.: US 9,834,522 B2
(45) Date of Patent: Dec. 5, 2017

(54) MULTI-FUNCTIONAL ACRYLATES

(71) Applicant: EMPIRE TECHNOLOGY DEVELOPMENT LLC, Wilmington, DE (US)

(72) Inventor: Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/768,217

(22) PCT Filed: Nov. 21, 2013

(86) PCT No.: PCT/US2013/071195
§ 371 (c)(1),
(2) Date: Aug. 15, 2015

(87) PCT Pub. No.: WO2014/126625
PCT Pub. Date: Aug. 21, 2014

(65) Prior Publication Data
US 2015/0376149 A1   Dec. 31, 2015

Related U.S. Application Data

(60) Provisional application No. 61/765,290, filed on Feb. 15, 2013.

(51) Int. Cl.

| | | |
|---|---|---|
| C07C 69/54 | (2006.01) | |
| C07D 251/70 | (2006.01) | |
| C07C 215/50 | (2006.01) | |
| C07C 233/38 | (2006.01) | |
| C08F 220/30 | (2006.01) | |
| C07D 251/54 | (2006.01) | |
| C08G 63/16 | (2006.01) | |
| C09D 167/02 | (2006.01) | |
| C08G 65/332 | (2006.01) | |
| C08F 222/10 | (2006.01) | |
| C09D 5/08 | (2006.01) | |

(52) U.S. Cl.
CPC ............ *C07D 251/70* (2013.01); *C07C 69/54* (2013.01); *C07C 215/50* (2013.01); *C07C 233/38* (2013.01); *C07D 251/54* (2013.01); *C08F 220/30* (2013.01); *C08F 222/1006* (2013.01); *C08G 63/16* (2013.01); *C08G 65/3322* (2013.01); *C09D 5/08* (2013.01); *C09D 167/02* (2013.01)

(58) Field of Classification Search
CPC .................................................. C07C 69/54
See application file for complete search history.

(56) References Cited

U.S. PATENT DOCUMENTS

| | | | | |
|---|---|---|---|---|
| 3,908,644 A | * | 9/1975 | Neinart | A43D 1/022 602/8 |
| 4,490,774 A | | 12/1984 | Olson et al. | |
| 4,515,931 A | | 5/1985 | Olson et al. | |
| 4,610,810 A | * | 9/1986 | Hasegawa | C08F 20/30 252/511 |
| 5,328,973 A | | 7/1994 | Roeschert et al. | |
| 5,663,264 A | | 9/1997 | Kawal et al. | |
| 5,710,281 A | | 1/1998 | Thurber et al. | |
| 6,126,837 A | * | 10/2000 | Miknevich | C02F 1/56 209/5 |

FOREIGN PATENT DOCUMENTS

EP   0718334 A1   6/1996

OTHER PUBLICATIONS

International Search Report for International Application No. PCT/US2013/071195 dated May 15, 2014.
Agriculture for Development, World development Report, The World Bank, Washington, DC (2008).
Ding et al. Synthesis and Adhesive Performances of Phenol Hydroxymethyl Acrylate, pp. 159-164 (Apr. 2003) (English abstract).
Kiatkamjornwong, Superabsorbent Polymers and Superabsorbent Polymer Composites, *ScienceAsia 33, Supplement 1* (Jan. 2007), pp. 39-43.
PERP Program—New Report Alert, Nexant Chem Systems, pp. 1-6, Nexant, Inc. (Apr. 2004).
Roper, Case Study 15.1?Water-repellent sands, accessed at http://sci-wikibook.bacs.uq.edu.au/?q=content/case-study-15-1-water-repellent-sands, accessed on Aug. 10, 2015, pp. 1-3.
Roper, Managing soils to enhance the potential for bioremediation of water repellency, *Australian Journal of Soil Research* (Nov. 9, 2005), 43(7):803-810.
Vinyl Polymers, accessed at http://web.archive.org/web/20121223015818/http://www.aqueroco.com/vinylpol.html, accessed on Aug. 11, 2015, pp. 1-2.
Li et al., Study on Synthesis of Anaerobic Adhesive, Productivity Assistance Centre of Tai'an County (Jun. 2009), 38(6) pp. 378-381.

\* cited by examiner

*Primary Examiner* — Michael Pepitone
(74) *Attorney, Agent, or Firm* — Pepper Hamilton LLP

(57) ABSTRACT

Disclosed herein are derivatives of phenolic and melamine compounds, methods of making these derivatives, and methods of using them. The compounds include phenolic and melamine compounds with multi-functional acrylate groups, polyethylene glycol and amino groups. The compounds may be cured to form resins that may be used in a variety of applications, such as paints, hydrogels, polyacrylate super absorbent polymers (SAPs), adhesives, composites, sealants, fillers, fire retardants, crosslinking agents, and the like.

10 Claims, No Drawings

MULTI-FUNCTIONAL ACRYLATES

CROSS-REFERENCE TO RELATED APPLICATIONS

This application is a U.S. national stage filing under 35 U.S.C. §371 of International Application No. PCT/US2013/071195 filed on Nov. 21, 2013 which claims the benefit of and priority to U.S. Provisional Application Ser. No. 61/765,290, entitled "Multi-Functional Acrylates," filed on Feb. 15, 2013. The aforementioned applications are incorporated by reference herein in its entirety and for all purposes.

BACKGROUND

Acrylate polymers are well known in commerce, and can be formed by polymerization of one or more acrylate esters such as methyl methacrylates. These acrylates can be used in various products, such as in hydrogels, polyacrylate super absorbent polymers (SAPs), emulsions, coatings, adhesives, sealants, and crosslinking agents. Such products can have good hydrolytic stability and other weathering characteristics, particularly when compared to polyesters and polyethers. Although acrylates are used widely, it will be desirable to develop acrylates with improved mechanical, physical and/or chemical properties. Such improved properties could result in products that have enhanced resistance to hostile environments such as those caused by, for example, acid rain, air-borne chemicals, cleaners used for dirt removal, erosion due to dirt particles or other debris, or actinic energy such as from sunlight, and the like.

SUMMARY

Disclosed herein are compositions of multi-functional acrylates, and methods of making such acrylates. The acrylates and polymers thereof can have a variety of attractive properties, such as high reactivity, high thermal stability, and high glass transition temperature. In one embodiment, a compound is of formula I

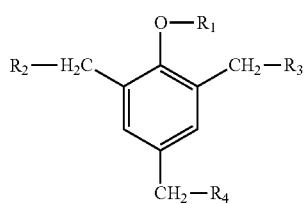

(I)

wherein:

$R_1$ is H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH$_2$—CH$_2$—O)$_n$H, where each n is, independently, an integer from 1 to 18;

$R_2$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_p$H, —(CH$_2$—CH$_2$—CH$_2$—O)$_p$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each p is, independently, an integer from 1 to 18;

$R_3$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each q is, independently, an integer from 1 to 18; and $R_4$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each r is, independently, an integer from 1 to 18.

In an additional embodiment, a compound is of formula II

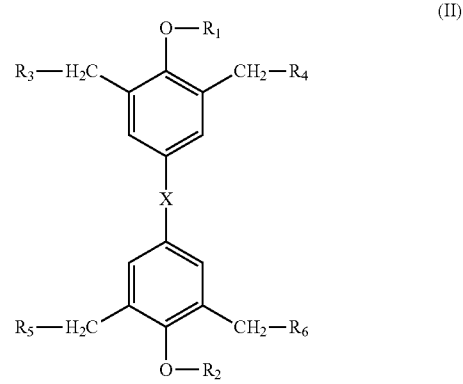

(II)

wherein:

$R_1$ is H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH$_2$—CH$_2$—O)$_n$H, where each n is, independently, an integer from 1 to 18;

$R_2$ is H, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH$_2$—CH$_2$—O)$_p$H, where each p is, independently, an integer from 1 to 18;

$R_3$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each q is, independently, an integer from 1 to 18;

$R_4$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each r is, independently, an integer from 1 to 18;

$R_5$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_s$H, —(CH$_2$—CH$_2$—CH$_2$—O)$_s$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each s is, independently, an integer from 1 to 18;

$R_6$ is —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each t is, independently, an integer from 1 to 18; and X is —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—.

In a further embodiment, a compound is of formula III

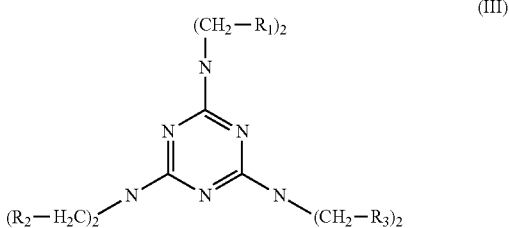

(III)

wherein:
each $R_1$ is, independently, —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_n$H, —(CH$_2$—CH$_2$—CH$_2$—O)$_n$H, —N[CH$_2$—CH$_2$—O—C(=O)—CH=CH$_2$]$_2$, —N[CH$_2$O—C(=O)—CH=CH$_2$]$_2$, —(CH$_2$—CH$_2$—O)$_n$—(CH$_2$—CH$_2$—CH$_2$—O)$_n$H, —N[CH$_2$—CH$_2$—NH—C(=O)—CH=CH$_2$]$_2$, or —NH—C(=O)CH=CH$_2$, where each n is, independently, an integer from 1 to 18;

each $R_2$ is, independently, —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, —N[CH$_2$—OC(=O)—CH=CH$_2$]$_2$, —N[CH$_2$—CH$_2$—O—C(=O)—CH=CH$_2$]$_2$, —(CH$_2$—CH$_2$—O)$_p$—(CH$_2$—CH$_2$—CH$_2$—O)$_p$H, —N[CH$_2$—CH$_2$—NH—C(=O)—CH=CH$_2$]$_2$, or —NH—C(=O)CH=CH$_2$, where each p is, independently, an integer from 1 to 18; and each $R_3$ is, independently, —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, —N[CH$_2$—OC(=O)—CH=CH$_2$]$_2$, —N[CH$_2$—CH$_2$—O—C(=O)—CH=CH$_2$]$_2$, —(CH$_2$—CH$_2$—O)$_q$—(CH$_2$—CH$_2$—CH$_2$—O)$_q$H, —N[CH$_2$—CH$_2$—NH—C(=O)—CH=CH$_2$]$_2$, or —NHC(=O)CH=CH$_2$, where each q is, independently, an integer from 1 to 18.

In an additional embodiment, a compound is of formula IV

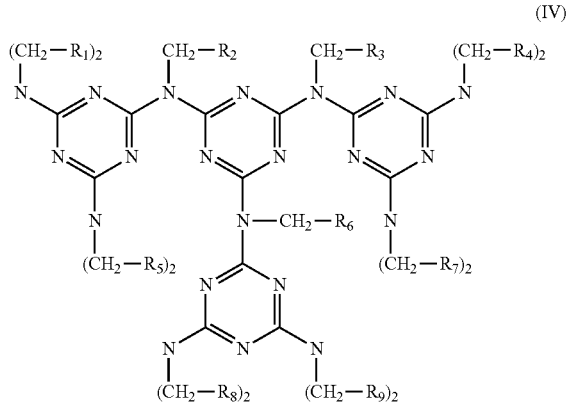

(IV)

wherein:
each $R_1$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_n$H, —(CH$_2$—CH$_2$—CH$_2$—O)$_n$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each n is, independently, an integer from 1 to 18;

$R_2$ is —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where p is an integer from 1 to 18;

$R_3$ is —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where q is an integer from 1 to 18;

each $R_4$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_r$H, —(CH$_2$—CH$_2$—CH$_2$—O)$_r$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each r is, independently, an integer from 1 to 18;

each $R_5$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_t$H, —(CH$_2$—CH$_2$—CH$_2$—O)$_t$H, —N[CH$_2$O—C(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each t is, independently, an integer from 1 to 18;

$R_6$ is —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_v$H, —(CH$_2$—CH$_2$—CH$_2$—O)$_v$H, —N[CH$_2$O—C(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where v is an integer from 1 to 18;

each $R_7$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_w$H, —(CH$_2$—CH$_2$—CH$_2$—O)$_w$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each w is, independently, an integer from 1 to 18;

each $R_8$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_y$H, —(CH$_2$—CH$_2$—CH$_2$—O)$_y$H, —N[CH$_2$O—C(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each y is, independently, an integer from 1 to 18; and each $R_9$ is, independently, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_z$H, —(CH$_2$—CH$_2$—CH$_2$—O)$_z$H, —N[CH$_2$OC(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, where each z is, independently, an integer from 1 to 18.

In a further embodiment, a coating composition may comprise any one or more of the compounds of any one or more of the following: formula I, formula II, formula III or formula IV.

In one embodiment, a hydrogel composition may comprise any one or more of the compounds of any one or more of the following: formula I, formula II, formula III or formula IV.

In an additional embodiment, a method of preparing a compound may comprise: (a) contacting a phenolic compound or a melamine compound with formaldehyde to form a hydroxymethyl compound; and (b) contacting the hydroxymethyl compound with an acrylic compound to form the compound.

DETAILED DESCRIPTION

This disclosure is not limited to the particular compounds, compositions, and methods described, as these may vary. The terminology used in the description is for the purpose of describing the particular versions or embodiments only, and is not intended to limit the scope.

Disclosed herein are compositions and compounds of multi-functional acrylates that display high reactivity, high thermal stability, and high glass transition temperature, and methods of making such acrylates. In some embodiments, a compound may be of formula I

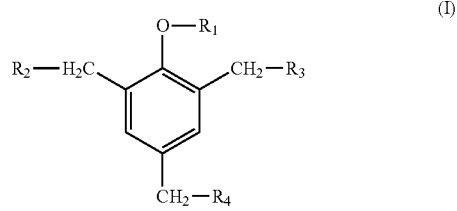

(I)

In some embodiments, $R_1$ may be H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)—(CH$_2$—CH$_2$—CH$_2$—O)$_n$H, where each n is, independently, an integer from 1 to 18. In some embodiments, $R_1$ may be H, —C(=O)—CH=CH$_2$, or —(CH$_2$—CH$_2$—O)$_n$H. In some embodiments, $R_1$ may be —C(=O)—CH=CH$_2$, —(CH$_2$—CH$_2$—O)$_n$H, or —(CH$_2$—CH$_2$—O)—(CH$_2$—CH$_2$—CH$_2$—O)$_n$H. In some embodiments, $R_1$ may be H or —C(=O)—CH=CH$_2$.

In some embodiments, $R_2$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_p$H, —(CH$_2$—CH$_2$—CH$_2$—O)$_p$H, —N[CH$_2$—CH$_2$—O—C(=O)—CH=CH$_2$]$_2$, N[CH$_2$—CH$_2$—NH—C(=O)—CH=CH$_2$]$_2$, or —NH—C(=O)CH=CH$_2$ where each p is, independently, an integer from 1 to 18. In some embodiments, $R_2$ may be —N(CH$_2$—CH$_2$—NH$_2$)$_2$, —O—C(=O)—CH=CH$_2$, —N[CH$_2$O—C(=O)—CH=CH$_2$]$_2$, —N[CH$_2$O—C(=O)—CH=CH$_2$]$_2$, —(CH$_2$—CH$_2$—O)$_p$H, or —(CH$_2$—CH$_2$—CH$_2$—O)$_p$H. In some embodiments, $R_2$ may be —N(CH$_2$—CH$_2$—NH$_2$)$_2$, —O—C(=O)—CH=CH$_2$, or —N[CH$_2$O—C(=O)—CH=CH$_2$]$_2$.

In some embodiments, $R_3$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each q is, independently, an integer from 1 to 18. In some embodiments, $R_3$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, or —(CH$_2$—CH$_2$—CH$_2$—O)$_q$H. In some embodiments, $R_3$ may be —N(CH$_2$—CH$_2$—NH$_2$)$_2$, —O—C(=O)—CH=CH$_2$, or —N[CH$_2$O—C(=O)—CH=CH$_2$]$_2$.

In some embodiments, $R_4$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each r is, independently, an integer from 1 to 18. In some embodiments, $R_4$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, or —(CH$_2$—CH$_2$—CH$_2$—O)$_r$H. In some embodiments, $R_4$ may be —N(CH$_2$—CH$_2$—NH$_2$)$_2$, —O—C(=O)—CH=CH$_2$, or —N[CH$_2$O—C(=O)—CH=CH$_2$]$_2$.

In some embodiments, the compound of formula I may have the following substitutions at each of, independently, $R_1$, $R_2$, $R_3$ and $R_4$, as shown in Table 1:

TABLE 1

| $R_1$ | $R_2$ | $R_3$ | $R_4$ |
|---|---|---|---|
| H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$(CH$_2$—CH$_2$—CH$_2$—O)$_n$H, where each n is, independently, an integer from 1 to 18. | —N(CH$_2$—CH$_2$—NH$_2$)$_2$, —O—C(=O)—CH=CH$_2$, —N[CH$_2$O—C(=O)CH=CH$_2$]$_2$, —(CH$_2$—CH$_2$—O)$_p$H, —(CH$_2$—CH$_2$—CH$_2$—O)$_p$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)—CH=CH$_2$ where each p is, independently, an integer from 1 to 18. | —N(CH$_2$—CH$_2$—NH$_2$)$_2$, —O—C(=O)—CH=CH$_2$, —N[CH$_2$O—C(=O)CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)—CH=CH$_2$ where each q is, independently, an integer from 1 to 18. | —N(CH$_2$—CH$_2$—NH$_2$)$_2$, —O—C(=O)—CH=CH$_2$, —N[CH$_2$O—C(=O)CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)—CH=CH$_2$ where each r is, independently, an integer from 1 to 18. |
| —C(=O)—CH=CH$_2$, —(CH$_2$—CH$_2$—O)$_n$H, or —(CH$_2$—CH$_2$—O)$_n$—(CH$_2$—CH$_2$—CH$_2$—O)$_n$H, where each n is, independently, an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_p$H, or —NH—C(=O)—CH=CH$_2$ where p is an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, or —NH—C(=O)—CH=CH$_2$ where q is an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, or —NH—C(=O)—CH=CH$_2$ where r is an integer from 1 to 18. |
| —C(=O)—CH=CH$_2$, —(CH$_2$—CH$_2$—O)$_n$H, or —(CH$_2$—CH$_2$—O)$_n$— | —N(CH$_2$—CH$_2$—NH$_2$)$_2$, —O—C(=O)—CH=CH$_2$, —N[CH$_2$O—C(=O)— | —N(CH$_2$—CH$_2$—NH$_2$)$_2$, —O—C(=O)—CH=CH$_2$, —N[CH$_2$OC(=O)— | —N(CH$_2$—CH$_2$—NH$_2$)$_2$, —O—C(=O)—CH=CH$_2$, —N[CH$_2$OC(=O)— |

TABLE 1-continued

| R$_1$ | R$_2$ | R$_3$ | R$_4$ |
|---|---|---|---|
| $(CH_2-CH_2-CH_2-O)_nH$, where each n is, independently, an integer from 1 to 18. | $CH=CH_2]_2$, or $-NH-C(=O)-CH=CH_2$ | $CH=CH_2]_2$, or $-NH-C(=O)-CH=CH_2$ | $CH=CH_2]_2$, or $-NH-C(=O)-CH=CH_2$ |
| H or $-(CH_2-CH_2-O)_nH$, where n is an integer from 1 to 18. | $-O-C(=O)-CH=CH_2$, or $-(CH_2-CH_2-O)_pH$, where p is an integer from 1 to 18. | $-O-C(=O)-CH=CH_2$ or $-(CH_2-CH_2-O)_qH$, where q is an integer from 1 to 18 | $-O-C(=O)-CH=CH_2$ or $-(CH_2-CH_2-O)_rH$, where r is an integer from 1 to 18 |
| $-(CH_2-CH_2-CH_2-O)_nH$, where n is an integer from 1 to 18. | $-O-C(=O)-CH=CH_2$ | $-O-C(=O)-CH=CH_2$ | $-O-C(=O)-CH=CH_2$ |
| $-(CH_2-CH_2-O)_nH$, where n is an integer from 1 to 18. | $-N[CH_2O-C(=O)-CH=CH_2]_2$, or $-NH-C(=O)-CH=CH_2$ | $-N[CH_2O-C(=O)-CH=CH_2]_2$, or $-NH-C(=O)-CH=CH_2$ | $-N[CH_2O-C(=O)-CH=CH_2]_2$, or $-NH-C(=O)-CH=CH_2$ |
| H | $-N[CH_2O-C(=O)-CH=CH_2]_2$, or $-NH-C(=O)-CH=CH_2$ $-O-C(=O)-CH=CH_2$ | $-N[CH_2O-C(=O)-CH=CH_2]_2$, or $-NH-C(=O)-CH=CH_2$ $-O-C(=O)-CH=CH_2$ | $-N[CH_2O-C(=O)-CH=CH_2]_2$, or $-NH-C(=O)-CH=CH_2$ $-O-C(=O)-CH=CH_2$ |
| H $-(CH_2-CH_2-CH_2-O)_nH$, where n is an integer from 1 to 18. | $-N[CH_2O-C(=O)-CH=CH_2]_2$, or $-NH-C(=O)-CH=CH_2$ | $-N[CH_2O-C(=O)-CH=CH_2]_2$, or $-NH-C(=O)-CH=CH_2$ | $-N[CH_2O-C(=O)-CH=CH_2]_2$, or $-NH-C(=O)-CH=CH_2$ |
| $-(CH_2-CH_2-O)_nH$, where n is an integer from 1 to 18. | $-O-C(=O)-CH=CH_2$ | $-O-C(=O)-CH=CH_2$ | $-O-C(=O)-CH=CH_2$ |

Non-limiting examples of phenolic compounds represented by formula I include, but are not limited to, the following compounds:

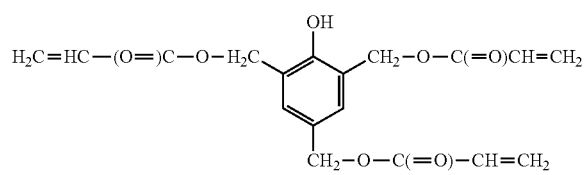

1

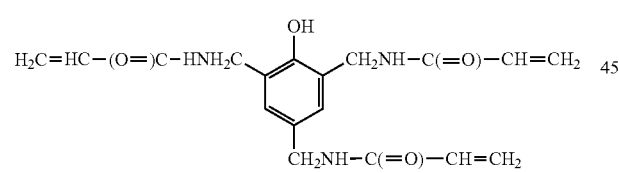

2

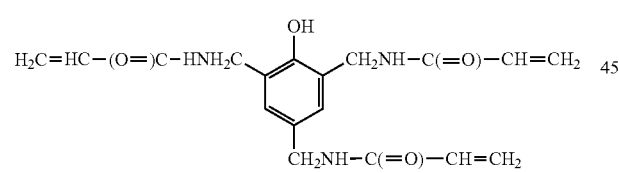

3

4

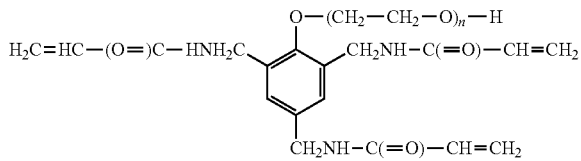

5

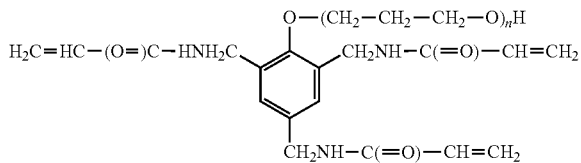

6

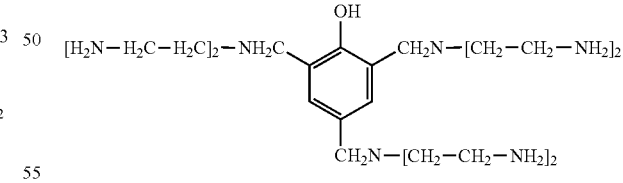

7

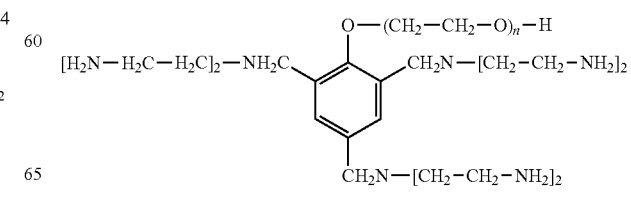

8

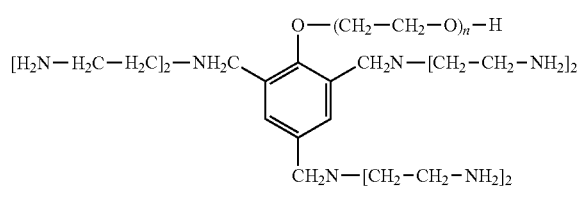

In some embodiments, a compound may be of formula II

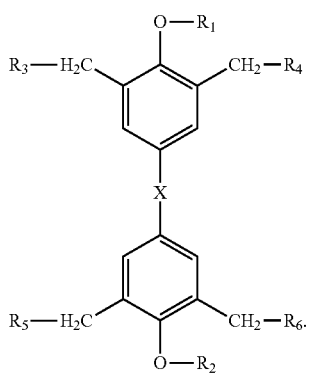

(II)

In some embodiments, $R_1$ may be H, —C(=O)—CH=CH$_2$, —(CH$_2$—CH$_2$—O)$_n$H, —(CH$_2$—CH$_2$—CH$_2$O)$_n$H, —(CH$_2$—CH$_2$—O)$_n$—(CH$_2$—CH$_2$—CH$_2$—O)$_n$H, where each n is, independently, an integer from 1 to 18. In some embodiments, $R_1$ may be H, —C(=O)—CH=CH$_2$, —(CH$_2$—CH$_2$—O)$_n$H, or —(CH$_2$—CH$_2$—CH$_2$—O)$_n$H. In some embodiments, $R_1$ may be H, —C(=O)—CH=CH$_2$, or —(CH$_2$—CH$_2$—O)$_n$H.

In some embodiments, $R_2$ may be H, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH$_2$—CH$_2$—O)$_p$H, where each p is, independently, an integer from 1 to 18. In some embodiments, $R_2$ may be H, —C(=O)—CH=CH$_2$, —(CH$_2$—CH$_2$—O)$_p$H, or —(CH$_2$—CH$_2$—CH$_2$—O)$_p$H. In some embodiments, $R_2$ may be H, —C(=O)—CH=CH$_2$, or —(CH$_2$—CH$_2$—O)$_p$H.

In some embodiments, $R_3$ may be —N(CH$_2$—CH$_2$—NH$_2$)$_2$, —O—C(=O)—CH=CH$_2$, —N[CH$_2$OC(=O)—CH=CH$_2$]$_2$, —(CH$_2$—CH$_2$—O)$_q$H, —(CH$_2$—CH$_2$—CH$_2$—O)$_q$H, N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each q is, independently, an integer from 1 to 18. In some embodiments, $R_3$ may be —N(CH$_2$—CH$_2$—NH$_2$)$_2$, —O—C(=O)—CH=CH$_2$, —N[CH$_2$OC(=O)—CH=CH$_2$]$_2$, —(CH$_2$—CH$_2$—O)$_q$H, or —(CH$_2$—CH$_2$—CH$_2$—O)$_q$H. In some embodiments, $R_3$ may be —N(CH$_2$—CH$_2$—NH$_2$)$_2$, —O—C(=O)—CH=CH$_2$, or —N[CH$_2$OC(=O)—CH=CH$_2$]$_2$. In some embodiments, $R_3$ may be —O—C(=O)—CH=CH$_2$ or —N(CH$_2$—CH$_2$—NH$_2$)$_2$.

In some embodiments, $R_4$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each r is, independently, an integer from 1 to 18. In some embodiments, $R_4$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, or —(CH$_2$—CH$_2$—CH$_2$—O)$_r$H. In some embodiments, $R_4$ may be —N(CH$_2$—CH$_2$—NH$_2$)$_2$, —O—C(=O)—CH=CH$_2$, or —N[CH$_2$O—C(=O)—CH=CH$_2$]$_2$. In some embodiments, $R_4$ may be —O—C(=O)—CH=CH$_2$ or —N(CH$_2$—CH$_2$—NH$_2$)$_2$.

In some embodiments, $R_5$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_s$H, —(CH$_2$—CH$_2$—CH$_2$—O)$_s$H, —N[CH$_2$—CH$_2$—O—C(=O)—CH=CH$_2$]$_2$, —N[CH$_2$—CH$_2$—NH—C(=O)—CH=CH$_2$]$_2$, or —NHC(=O)CH=CH2 where each s is, independently, an integer from 1 to 18. In some embodiments, $R_5$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_s$H, or —(CH$_2$—CH$_2$—CH$_2$—O)$_s$H. In some embodiments, $R_5$ may be —N(CH$_2$—CH$_2$—NH$_2$)$_2$, —O—C(=O)—CH=CH$_2$, or —N[CH$_2$O—C(=O)—CH=CH$_2$]$_2$. In some embodiments, $R_5$ may be —O—C(=O)—CH=CH$_2$ or —N(CH$_2$—CH$_2$—NH$_2$)$_2$.

In some embodiments, $R_6$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$ where each t is, independently, an integer from 1 to 18. In some embodiments, $R_6$ may be —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_t$H, or —(CH$_2$—CH$_2$—CH$_2$—O)H. In some embodiments, $R_6$ may be —N(CH$_2$—CH$_2$—NH$_2$)$_2$, —O—C(=O)—CH=CH$_2$, or —N[CH$_2$O—C(=O)—CH=CH$_2$]$_2$. In some embodiments, $R_6$ may be —O—C(=O)—CH=CH$_2$ or —N(CH$_2$—CH$_2$—NH$_2$)$_2$.

In some embodiments, X may be —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—. In some embodiments, X may be —CH$_2$—, —C(CH$_3$)$_2$—, —S—, —S(=O)$_2$—, —S(=O)—, —CH(CCl$_3$), or —C(Cl)$_2$. In some embodiments, X may be —CH$_2$—, —C(CH$_3$)$_2$—, —S—, —S(=O)$_2$—, or —S(=O)—. In some embodiments, X may be —CH$_2$—, —C(CH$_3$)$_2$—, —S—, —CH(CCl$_3$)—, or —C(Cl)$_2$—.

In some embodiments, compounds of formula II may have the following substitutions at each of, independently, X, $R_1$, $R_2$, $R_3$, $R_4$, $R_5$ and $R_6$, as shown in Table 2:

TABLE 2

| X | $R_1$ | $R_2$ |
|---|---|---|
| —CH$_2$— | —H,<br>—C(=O)—CH=CH$_2$,<br>—(CH$_2$—CH$_2$—O)$_n$H,<br>—(CH$_2$—CH$_2$—CH$_2$—O)$_n$H,<br>or<br>(CH$_2$—CH$_2$—O)$_n$—(CH$_2$—CH$_2$—CH$_2$—O)$_n$H,<br>where each n is,<br>independently,<br>an integer from<br>1 to 18. | —H,<br>—C(=O)—CH=CH$_2$,<br>—(CH$_2$—CH$_2$—O)$_p$H,<br>—(CH$_2$—CH$_2$—CH$_2$—O)$_p$H,<br>or<br>—(CH$_2$—CH$_2$—O)$_p$—(CH$_2$—CH$_2$—CH$_2$—O)$_p$H,<br>where each p is,<br>independently,<br>an integer from<br>1 to 18. |
| —CH$_2$— | —C(=O)—CH=CH$_2$,<br>or<br>—(CH$_2$—CH$_2$—O)$_n$H, | —C(=O)—CH=CH$_2$,<br>or<br>—(CH$_2$—CH$_2$—O)$_p$H, |

TABLE 2-continued

| | |
|---|---|
| —CH₂— | where n is an integer from 1 to 18. |
| —CH₂— | —H, —C(=O)—CH=CH₂, or —(CH₂—CH₂—O)ₙH, where n is an integer from 1 to 18. |
| —CH₂— | —H, or —(CH₂—CH₂—O)ₙH, where n is an integer from 1 to 18. |
| —CH₂— | —H |
| —CH₂— | —H |
| —CH₂— | —H |
| —CH₂— | —(CH₂—CH₂—O)ₙH, where n is an integer from 1 to 18. |
| —CH₂— | —(CH₂—CH₂—O)ₙH, where n is an integer from 1 to 18. |
| —CH₂— | —(CH₂—CH₂—CH₂—O)ₙH, where n is an integer from 1 to 18. |
| —CH₂— | —(CH₂—CH₂—CH₂—O)ₙH, where n is an integer from 1 to 18. |
| —CH₂— | —C(=O)—CH=CH₂ |
| —CH₂— | —(CH₂—CH₂—O)ₙH, where n is an integer from 1 to 18. |
| —CH₂— | —(CH₂—CH₂—CH₂—O)ₙH, where n is an integer from 1 to 18. |

| | |
|---|---|
| | where p is an integer from 1 to 18. |
| | —H, —C(=O)—CH=CH₂, or —(CH₂—CH₂—O)ₚH, where p is an integer from 1 to 18. |
| | —H, or —(CH₂—CH₂—O)ₚH, where p is an integer from 1 to 18. |
| | —H |
| | —H |
| | —H |
| | —(CH₂—CH₂—O)ₚH, where p is an integer from 1 to 18. |
| | —(CH₂—CH₂—O)ₚH, where p is an integer from 1 to 18. |
| | —(CH₂—CH₂—CH₂—O)ₚH, where p is an integer from 1 to 18. |
| | —(CH₂—CH₂—CH₂—O)ₚH, where p is an integer from 1 to 18. |
| | —C(=O)—CH=CH₂ |
| | —(CH₂—CH₂—O)ₚH, where p is an integer from 1 to 18. |
| | —(CH₂—CH₂—CH₂—O)ₚH, where p is an integer from 1 to 18. |

| R₃ | R₄ |
|---|---|
| —N(CH₂—CH₂—NH₂)₂, —O—C(=O)—CH=CH₂, —N[CH₂O—C(=O)—CH=CH₂]₂, —(CH₂—CH₂—O)qH, —(CH₂—CH₂—CH₂—O)qH, —N[CH₂—CH₂—O—C(=O)—CH=CH₂]₂, —N[CH₂—CH₂—NH—C(=O)—CH=CH₂]₂, or —NH—C(=O)—CH=CH2 where each q is, independently, an integer from 1 to 18. | —N(CH₂—CH₂—NH₂)₂, —O—C(=O)—CH=CH₂, —N[CH₂O—C(=O)—CH=CH₂]₂, —(CH₂—CH₂—O)ᵣH, —(CH₂—CH₂—CH₂—O)ᵣH, —N[CH₂—CH₂—O—C(=O)—CH=CH₂]₂, —N[CH₂—CH₂—NH—C(=O)—CH=CH₂]₂, or —NH—C(=O)—CH=CH₂ where each r is, independently, an integer from 1 to 18. |
| —O—C(=O)—CH=CH₂, —N[CH₂O—C(=O)—CH=CH₂]₂, —N[CH₂—CH₂—O—C(=O)—CH=CH₂]₂, or —NH—C(=O)—CH=CH₂ | —O—C(=O)—CH=CH₂, —N[CH₂O—C(=O)—CH=CH₂]₂, —N[CH₂—CH₂—O—C(=O)—CH=CH₂]₂, or —NH—C(=O)CH=CH₂ |
| —O—C(=O)—CH=CH₂, or —N(CH₂—CH₂—NH₂)₂. | —O—C(=O)—CH=CH₂, or —N(CH₂—CH₂—NH₂)₂. |
| —O—C(=O)—CH=CH₂ or —N(CH₂—CH₂—NH₂)₂. | —O—C(=O)—CH=CH₂ or —N(CH₂—CH₂—NH₂)₂. |
| —O—C(=O)—CH=CH₂ —N[CH₂O—C(=O)—CH=CH₂]₂ —N(CH₂—CH₂—NH₂)₂ —O—C(=O)—CH=CH₂ —N[CH₂O—C(=O)—CH=CH₂]₂ —N[CH₂O—C(=O)—CH=CH₂]₂ —O—C(=O)—CH=CH₂ —N[CH₂O—C(=O)—CH=CH₂]₂ | —O—C(=O)—CH=CH₂ —N[CH₂O—C(=O)—CH=CH₂]₂ —N(CH₂—CH₂—NH₂)₂ —O—C(=O)—CH=CH₂ —N[CH₂O—C(=O)—CH=CH₂]₂ —N[CH₂O—C(=O)—CH=CH₂]₂ —O—C(=O)—CH=CH₂ —N[CH₂O—C(=O)—CH=CH₂]₂ |

TABLE 2-continued

| —N[CH$_2$—CH$_2$—NH$_2$)$_2$ | —N[CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>or<br>—NH—C(=O)—CH=CH$_2$<br>where each s is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)CH=CH$_2$<br>—O—C(=O)—CH=CH$_2$,<br>or<br>—N(CH$_2$—CH$_2$—NH$_2$)$_2$.<br>—O—C(=O)—CH=CH$_2$<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N[CH$_2$—CH$_2$—NH$_2$)$_2$<br>—N(CH$_2$—CH$_2$—NH$_2$)$_2$ | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>or<br>—NH—C(=O)—CH=CH$_2$<br>where each t is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)CH=CH$_2$<br>—O—C(=O)—CH=CH$_2$,<br>or<br>—N(CH$_2$—CH$_2$—NH$_2$)$_2$.<br>—O—C(=O)—CH=CH$_2$<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N[CH$_2$—CH$_2$—NH$_2$)$_2$<br>—N(CH$_2$—CH$_2$—NH$_2$)$_2$ |

In some embodiments, compounds of formula II may have the following substitutions at each of, independently, X, R$_1$, R$_2$, R$_3$, R$_4$, R$_5$ and R$_6$, as shown in Table 3:

TABLE 3

| X | R$_1$ | R$_2$ |
|---|---|---|
| —C(CH$_3$)$_2$— | —H,<br>—C(=O)—CH=CH$_2$,<br>—(CH$_2$—CH$_2$—O)$_n$H,<br>—(CH$_2$—CH$_2$—CH$_2$—O)$_n$H,<br>or<br>—(CH$_2$—CH$_2$—O)$_n$—(CH$_2$—CH$_2$—CH$_2$—O)$_n$H,<br>where each n is, independently, an integer from 1 to 18. | —H,<br>—C(=O)—CH=CH$_2$,<br>—(CH$_2$—CH$_2$—O)$_p$H,<br>—(CH$_2$—CH$_2$—CH$_2$—O)$_p$H,<br>or<br>—(CH$_2$—CH$_2$—O)$_p$—(CH$_2$—CH$_2$—CH$_2$—O)$_p$H,<br>where each p is, independently, an integer from 1 to 18. |
| —C(CH$_3$)$_2$— | —C(=O)—CH=CH$_2$,<br>or<br>—(CH$_2$—CH$_2$—O)$_n$H,<br>where n is an integer from 1 to 18. | —C(=O)—CH=CH$_2$,<br>or<br>—(CH$_2$—CH$_2$—O)$_p$H,<br>where p is an integer from 1 to 18. |
| —C(CH$_3$)$_2$— | —H,<br>—C(=O)—CH=CH$_2$,<br>or<br>—(CH$_2$—CH$_2$—O)$_n$H,<br>where n is an integer from 1 to 18. | —H,<br>—C(=O)—CH=CH$_2$,<br>or<br>—(CH$_2$—CH$_2$—O)$_p$H,<br>where p is an integer from 1 to 18. |
| —C(CH$_3$)$_2$— | —H, or<br>—(CH$_2$—CH$_2$—O)$_n$H,<br>where n is an | —H, or<br>—(CH$_2$—CH$_2$—O)$_p$H,<br>where p is an |

TABLE 3-continued

| | | |
|---|---|---|
| —C(CH$_3$)$_2$— | integer from 1 to 18. | integer from 1 to 18. |
| —C(CH$_3$)$_2$— | —H | —H |
| —C(CH$_3$)$_2$— | —H | —H |
| —C(CH$_3$)$_2$— | —H | —H |
| —C(CH$_3$)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(CH$_3$)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(CH$_3$)$_2$— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |
| —C(CH$_3$)$_2$— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |
| —C(CH$_3$)$_2$— | —C(=O)—CH=CH$_2$ | —C(=O)—CH=CH$_2$ |
| —C(CH$_3$)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(CH$_3$)$_2$— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |

| R$_3$ | R$_4$ |
|---|---|
| —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O—CH=CH2 where each q is, independently, an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O—CH=CH$_2$ where each r is, independently, an integer from 1 to 18. |
| —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ | —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$ | —O—C(=O)—CH=CH$_2$ |
| —N[CH$_2$O—C(=O)—CH=CH$_2$]$_2$ | —N[CH$_2$O—C(=O)—CH=CH$_2$]$_2$ |
| —N(CH$_2$—CH$_2$—NH$_2$)$_2$ | —N(CH$_2$—CH$_2$—NH$_2$)$_2$ |
| —O—C(=O)—CH=CH$_2$ | —O—C(=O)CH=CH$_2$ |
| —N[CH$_2$O—C(=O)—CH=CH$_2$]$_2$ | —N[CH$_2$O—C(=O)—CH=CH$_2$]$_2$ |
| —N[CH$_2$O—C(=O)—CH=CH$_2$]$_2$ | —N[CH$_2$O—C(=O)—CH=CH$_2$]$_2$ |
| —O—C(=O)—CH=CH$_2$ | —O—C(=O)CH=CH$_2$ |
| —N[CH$_2$O—C(=O)—CH=CH$_2$]$_2$ | —N[CH$_2$O—C(=O)—CH=CH$_2$]$_2$ |
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

| R$_5$ | R$_6$ |
|---|---|
| —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_s$H, —(CH$_2$—CH$_2$—CH$_2$—O)$_s$H, —N[CH$_2$—CH$_2$—O—C(=O)—CH=CH$_2$]$_2$, or —N[CH$_2$—CH$_2$—NH—C(=O)—CH=CH$_2$]$_2$, or | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, or —N[CH$_2$—CH$_2$—NH—C(=O)—CH=CH$_2$]$_2$, or |

TABLE 3-continued

| | |
|---|---|
| —NH—C(=O)—CH=CH$_2$ where each s is, independently, an integer from 1 to 18. | —NH—C(=O)—CH=CH$_2$ where each t is, independently, an integer from 1 to 18. |
| —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ | —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$ —N[CH$_2$O—C(=O)—CH=CH$_2$]$_2$ —N(CH$_2$—CH$_2$—NH$_2$)$_2$ | —O—C(=O)—CH=CH$_2$ —N[CH$_2$O—C(=O)—CH=CH$_2$]$_2$ —N(CH$_2$—CH$_2$—NH$_2$)$_2$ |
| —O—C(=O)—CH=CH$_2$ —N[CH$_2$O—C(=O)—CH=CH$_2$]$_2$ —N[CH$_2$O—C(=O)—CH=CH$_2$]$_2$ | —O—C(=O)—CH=CH$_2$ —N[CH$_2$O—C(=O)—CH=CH$_2$]$_2$ —N[CH$_2$O—C(=O)—CH=CH$_2$]$_2$ |
| —O—C(=O)—CH=CH$_2$ —N[CH$_2$O—C(=O)—CH=CH$_2$]$_2$ —N(CH$_2$—CH$_2$—NH$_2$)$_2$ —N(CH$_2$—CH$_2$—NH$_2$)$_2$ | —O—C(=O)—CH=CH$_2$ —N[CH$_2$O—C(=O)—CH=CH$_2$]$_2$ —N(CH$_2$—CH$_2$—NH$_2$)$_2$ —N(CH$_2$—CH$_2$—NH$_2$)$_2$ |

In some embodiments, compounds of formula II may have the following substitutions at each of, independently, X, $R_1$, $R_2$, $R_3$, $R_4$, $R_5$ and $R_6$, as shown in Table 4:

TABLE 4

| X | $R_1$ | $R_2$ |
|---|---|---|
| —S— | —H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH$_2$—CH$_2$—O)$_n$H, where each n is, independently, an integer from 1 to 18. | —H, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH$_2$—CH$_2$—O)$_p$H, where each p is, independently, an integer from 1 to 18. |
| —S— | —C(=O)—CH=CH$_2$, or —(CH$_2$—CH$_2$—O)$_n$H, where n is an integer from 1 to 18. | —C(=O)—CH=CH$_2$, or —(CH$_2$—CH$_2$—O)$_p$H, where p is an integer from 1 to 18. |
| —S— | —H, —C(=O)—CH=CH$_2$, or —(CH$_2$—CH$_2$—O)$_n$H, where n is an integer from 1 to 18. | —H, —C(=O)—CH=CH$_2$, or —(CH$_2$—CH$_2$—O)$_p$H, where p is an integer from 1 to 18. |
| —S— | —H, or —(CH$_2$—CH$_2$—O)$_n$H, where n is an integer from 1 to 18. | —H, or —(CH$_2$—CH$_2$—O)$_p$H, where p is an integer from 1 to 18. |
| —S— | —H | —H |
| —S— | —H | —H |
| —S— | —H | —H |
| —S— | —(CH$_2$—CH$_2$—O)$_n$H, where n is an integer from 1 to 18. | —(CH$_2$—CH$_2$—O)$_p$H, where p is an integer from 1 to 18. |
| —S— | —(CH$_2$—CH$_2$—O)$_n$H, where n is an integer from 1 to 18. | —(CH$_2$—CH$_2$—O)$_p$H, where p is an integer from 1 to 18. |

TABLE 4-continued

| | |
|---|---|
| —S— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |
| —S— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |
| —S— | —C(=O)—CH=CH$_2$ | —C(=O)—CH=CH$_2$ |
| —S— | —(CH$_2$—CH$_2$—O)$_n$H, where n is an integer from 1 to 18. | —(CH$_2$—CH$_2$—O)$_p$H, where p is an integer from 1 to 18. |
| —S— | —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |

| R$_3$ | R$_4$ |
|---|---|
| —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_q$H, —(CH$_2$—CH$_2$—CH$_2$—O)$_q$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)—CH=CH2 where each q is, independently, an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)—CH=CH$_2$ where each r is, independently, an integer from 1 to 18. |
| —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ | —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$, or —N(CH$_2$—CH$_2$—NH$_2$)$_2$. | —O—C(=O)—CH=CH$_2$, or —N(CH$_2$—CH$_2$—NH$_2$)$_2$. |
| —O—C(=O)—CH=CH$_2$ —N[CH$_2$O—C(=O)—CH=CH$_2$]$_2$ —N(CH$_2$—CH$_2$—NH$_2$)$_2$ | —O—C(=O)—CH=CH$_2$ —N[CH$_2$O—C(=O)—CH=CH$_2$]$_2$ —N(CH$_2$—CH$_2$—NH$_2$)$_2$ |
| —O—C(=O)—CH=CH$_2$ —N[CH$_2$O—C(=O)—CH=CH$_2$]$_2$ —N[CH$_2$O—C(=O)—CH=CH$_2$]$_2$ —O—C(=O)—CH=CH$_2$ —N[CH$_2$O—C(=O)—CH=CH$_2$]$_2$ —N(CH$_2$—CH$_2$—NH$_2$)$_2$ —N(CH$_2$—CH$_2$—NH$_2$)$_2$ | —O—C(=O)—CH=CH$_2$ —N[CH$_2$O—C(=O)—CH=CH$_2$]$_2$ —N[CH$_2$O—C(=O)—CH=CH$_2$]$_2$ —O—C(=O)—CH=CH$_2$ —N[CH$_2$O—C(=O)—CH=CH$_2$]$_2$ —N(CH$_2$—CH$_2$—NH$_2$)$_2$ —N(CH$_2$—CH$_2$—NH$_2$)$_2$ |

| R$_5$ | R$_6$ |
|---|---|
| —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_s$H, —(CH$_2$—CH$_2$—CH$_2$—O)$_s$H, —N[CH$_2$—CH$_2$—O—C(=O)—CH=CH$_2$]$_2$, or —N[CH$_2$—CH$_2$—NH—C(=O)—CH=CH$_2$]$_2$, or —NH—C(=O)—CH=CH$_2$ where each s is, independently, an integer from 1 to 18. | —N(CH$_2$—CH$_2$—NH$_2$)$_2$, —O—C(=O)—CH=CH$_2$, —N[CH$_2$O—C(=O)—CH=CH$_2$]$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, or —N[CH$_2$—CH$_2$—NH—C(=O)—CH=CH$_2$]$_2$, or —NH—C(=O)—CH=CH$_2$ where each t is, independently, an integer from 1 to 18. |
| —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ —O—C(=O)—CH=CH$_2$, or | —O—C(=O)—CH=CH$_2$, —N[CH$_2$O—C(=O)—CH=CH$_2$]$_2$, —N[CH$_2$—CH$_2$—O—C(=O)—CH=CH$_2$]$_2$, or —NH—C(=O)—CH=CH$_2$ —O—C(=O)—CH=CH$_2$, or |

TABLE 4-continued

| | |
|---|---|
| —N(CH₂—CH₂—NH₂)₂. | —N(CH₂—CH₂—NH₂)₂. |
| —O—C(=O)—CH=CH₂, | —O—C(=O)—CH=CH₂, |
| or | or |
| —N(CH₂—CH₂—NH₂)₂. | —N(CH₂—CH₂—NH₂)₂. |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N(CH₂—CH₂—NH₂)₂ | —N(CH₂—CH₂—NH₂)₂ |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N[CH₂O—C(=O)—CH=CH₂]₂ | —N[CH₂O—C(=O)—CH=CH₂]₂ |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N(CH₂—CH₂—NH₂)₂ | —N(CH₂—CH₂—NH₂)₂ |
| —N(CH₂—CH₂—NH₂)₂ | —N(CH₂—CH₂—NH₂)₂ |

In some embodiments, compounds of formula II may have the following substitutions at each of, independently, X, $R_1$, $R_2$, $R_3$, $R_4$, $R_5$ and $R_6$, as shown in Table 5:

TABLE 5

| X | $R_1$ | $R_2$ |
|---|---|---|
| —S(=O)₂— | —H,<br>—C(=O)—CH=CH₂,<br>—(CH₂—CH₂—O)ₙH,<br>—(CH₂—CH₂—CH₂—O)ₙH,<br>or<br>—(CH₂—CH₂—O)ₙ—(CH₂—CH₂—CH₂—O)ₙH,<br>where each n is,<br>independently,<br>an integer from<br>1 to 18. | —H,<br>—C(=O)—CH=CH₂,<br>—(CH₂—CH₂—O)ₚH,<br>—(CH₂—CH₂—CH₂—O)ₚH,<br>or<br>—(CH₂—CH₂—O)ₚ—(CH₂—CH₂—CH₂—O)ₚH,<br>where each p is,<br>independently,<br>an integer from<br>1 to 18. |
| —S(=O)₂— | —C(=O)—CH=CH₂,<br>or<br>—(CH₂—CH₂—O)ₙH,<br>where n is an<br>integer from 1 to 18. | —C(=O)—CH=CH₂,<br>or<br>—(CH₂—CH₂—O)ₚH,<br>where p is an<br>integer from 1 to 18. |
| —S(=O)₂— | —H,<br>—C(=O)—CH=CH₂,<br>or<br>—(CH₂—CH₂—O)ₙH,<br>where n is an<br>integer from 1 to 18. | —H,<br>—C(=O)—CH=CH₂,<br>or<br>—(CH₂—CH₂—O)ₚH,<br>where p is an<br>integer from 1 to 18. |
| —S(=O)₂— | —H, or<br>—(CH₂—CH₂—O)ₙH,<br>where n is an<br>integer from 1 to 18. | —H, or<br>—(CH₂—CH₂—O)ₚH,<br>where p is an<br>integer from 1 to 18. |
| —S(=O)₂— | —H | —H |
| —S(=O)₂— | —H | —H |
| —S(=O)₂— | —H | —H |
| —S(=O)₂— | —(CH₂—CH₂—O)ₙH,<br>where n is<br>an integer from<br>1 to 18. | —(CH₂—CH₂—O)ₚH,<br>where p is<br>an integer from<br>1 to 18. |
| —S(=O)₂— | —(CH₂—CH₂—O)ₙH,<br>where n is<br>an integer from<br>1 to 18. | —(CH₂—CH₂—O)ₚH,<br>where p is<br>an integer from<br>1 to 18. |
| —S(=O)₂— | —(CH₂—CH₂—CH₂—O)ₙH,<br>where n is an<br>integer from 1 to 18. | —(CH₂—CH₂—CH₂—O)ₚH,<br>where p is an<br>integer from 1 to 18. |
| —S(=O)₂— | —(CH₂—CH₂—CH₂—O)ₙH,<br>where n is an<br>integer from 1 to 18. | —(CH₂—CH₂—CH₂—O)ₚH,<br>where p is an<br>integer from 1 to 18. |
| —S(=O)₂— | —C(=O)—CH=CH₂ | —C(=O)—CH=CH₂ |
| —S(=O)₂— | —(CH₂—CH₂—O)ₙH,<br>where n is<br>an integer from<br>1 to 18. | —(CH₂—CH₂—O)ₚH,<br>where p is<br>an integer from<br>1 to 18. |

TABLE 5-continued

| | |
|---|---|
| —S(=O)$_2$— —(CH$_2$—CH$_2$—CH$_2$—O)$_n$H, where n is an integer from 1 to 18. | —(CH$_2$—CH$_2$—CH$_2$—O)$_p$H, where p is an integer from 1 to 18. |

| R$_3$ | R$_4$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_q$H,<br>—(CH$_2$—CH$_2$—CH$_2$—O)$_q$H,<br>—N[CH$_2$—CH$_2$—O—C(=O)—CH=CH$_2$]$_2$,<br>—N[CH$_2$—CH$_2$—NH—C(=O)—CH=CH$_2$]$_2$,<br>or<br>—NH—C(=O)—CH=CH2<br>where each q is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)—CH=CH$_2$<br>—O—C(=O)—CH=CH$_2$,<br>or<br>—N(CH$_2$—CH$_2$—NH$_2$)$_2$.<br>—O—C(=O)—CH=CH$_2$,<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$,<br>—N[CH$_2$—CH$_2$—NH—C(=O)—CH=CH$_2$]$_2$,<br>or<br>—NH—C(=O)—CH=CH$_2$<br>where each r is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)—CH=CH$_2$<br>—O—C(=O)—CH=CH$_2$,<br>or<br>—N(CH$_2$—CH$_2$—NH$_2$)$_2$.<br>—O—C(=O)—CH=CH$_2$,<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>or<br>—NH—C(=O)—CH=CH$_2$<br>where each s is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)—CH=CH$_2$<br>—O—C(=O)—CH=CH$_2$,<br>or<br>—N(CH$_2$—CH$_2$—NH$_2$)$_2$.<br>—O—C(=O)—CH=CH$_2$,<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$ | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>or<br>—NH—C(=O)—CH=CH$_2$<br>where each t is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$,<br>or<br>—NH—C(=O)—CH=CH$_2$<br>—O—C(=O)—CH=CH$_2$,<br>or<br>—N(CH$_2$—CH$_2$—NH$_2$)$_2$.<br>—O—C(=O)—CH=CH$_2$,<br>or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$ |

TABLE 5-continued

| | |
|---|---|
| —N[CH$_2$O—C(=O)—CH=CH$_2$]$_2$ | —N[CH$_2$O—C(=O)—CH=CH$_2$]$_2$ |
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

In some embodiments, compounds of formula II may have the following substitutions at each of, independently, X, $R_1$, $R_2$, $R_3$, $R_4$, $R_5$ and $R_6$, as shown in Table 6:

TABLE 6

| X | $R_1$ | $R_2$ |
|---|---|---|
| —S(=O)— | —H,<br>—C(=O)—CH=CH$_2$,<br>—(CH$_2$—CH$_2$—O)$_n$H,<br>—(CH$_2$—CH$_2$—CH$_2$—O)$_n$H,<br>or<br>—(CH$_2$—CH$_2$—O)$_n$—(CH$_2$—CH$_2$—CH$_2$—O)$_n$H,<br>where each n is, independently, an integer from 1 to 18. | —H,<br>—C(=O)—CH=CH$_2$,<br>—(CH$_2$—CH$_2$—O)$_p$H,<br>—(CH$_2$—CH$_2$—CH$_2$—O)$_p$H,<br>or<br>—(CH$_2$—CH$_2$—O)$_p$—(CH$_2$—CH$_2$—CH$_2$—O)$_p$H,<br>where each p is, independently, an integer from 1 to 18. |
| —S(=O)— | —C(=O)—CH=CH$_2$,<br>or<br>—(CH$_2$—CH$_2$—O)$_n$H,<br>where n is an integer from 1 to 18. | —C(=O)—CH=CH$_2$,<br>or<br>—(CH$_2$—CH$_2$—O)$_p$H,<br>where n is an integer from 1 to 18. |
| —S(=O)— | —H,<br>—C(=O)—CH=CH$_2$,<br>or<br>—(CH$_2$—CH$_2$—O)$_n$H,<br>where n is an integer from 1 to 18. | —H,<br>—C(=O)—CH=CH$_2$,<br>or<br>—(CH$_2$—CH$_2$—O)$_p$H,<br>where p is an integer from 1 to 18. |
| —S(=O)— | —H, or<br>—(CH$_2$—CH$_2$—O)$_n$H,<br>where n is an integer from 1 to 18. | —H, or<br>—(CH$_2$—CH$_2$—O)$_p$H,<br>where p is an integer from 1 to 18. |
| —S(=O)— | —H | —H |
| —S(=O)$_2$— | —H | —H |
| —S(=O)— | —H | —H |
| —S(=O)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —S(=O)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —S(=O)— | —(CH$_2$—CH$_2$—CH$_2$—O)$_n$H,<br>where n is an integer from 1 to 18. | —(CH$_2$—CH$_2$—CH$_2$—O)$_p$H,<br>where p is an integer from 1 to 18. |
| —S(=O)— | —(CH$_2$—CH$_2$—CH$_2$—O)$_n$H,<br>where n is an integer from 1 to 18. | —(CH$_2$—CH$_2$—CH$_2$—O)$_p$H,<br>where p is an integer from 1 to 18. |
| —S(=O)— | —C(=O)—CH=CH$_2$ | —C(=O)—CH=CH$_2$ |
| —S(=O)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —S(=O)— | —(CH$_2$—CH$_2$—CH$_2$—O)$_n$H,<br>where n is an integer from 1 to 18. | —(CH$_2$—CH$_2$—CH$_2$—O)$_p$H,<br>where p is an integer from 1 to 18. |

| $R_3$ | $R_4$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_q$H,<br>—(CH$_2$—CH$_2$—CH$_2$—O)$_q$H,<br>—N[CH$_2$—CH$_2$—O—C(=O)—CH=CH$_2$]$_2$, | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$, |

TABLE 6-continued

| | |
|---|---|
| —N[CH$_2$—CH$_2$—NH—C(=O)—CH=CH$_2$]$_2$, or<br>—NH—C(=O)—CH=CH2<br>where each q is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$<br>—O—C(=O)—CH=CH$_2$, or<br>—N(CH$_2$—CH$_2$—NH$_2$)$_2$.<br>—O—C(=O)—CH=CH$_2$, or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ | —N[CH$_2$—CH$_2$—NH—C(=O)—CH=CH$_2$]$_2$, or<br>—NH—C(=O)—CH=CH$_2$<br>where each r is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$<br>—O—C(=O)—CH=CH$_2$, or<br>—N(CH$_2$—CH$_2$—NH$_2$)$_2$.<br>—O—C(=O)—CH=CH$_2$, or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each s is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$<br>—O—C(=O)—CH=CH$_2$, or<br>—N(CH$_2$—CH$_2$—NH$_2$)$_2$.<br>—O—C(=O)—CH=CH$_2$, or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each t is, independently, an integer from 1 to 18.<br>—O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$<br>—O—C(=O)—CH=CH$_2$, or<br>—N(CH$_2$—CH$_2$—NH$_2$)$_2$.<br>—O—C(=O)—CH=CH$_2$, or<br>—N(CH$_2$—CH$_2$—NH$_2$)$_2$.<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ |

TABLE 6-continued

| | |
|---|---|
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

In some embodiments, compounds of formula II may have the following substitutions at each of, independently, X, $R_1$, $R_2$, $R_3$, $R_4$, $R_5$ and $R_6$, as shown in Table 7:

TABLE 7

| X | $R_1$ | $R_2$ |
|---|---|---|
| —CH(CCl$_3$)— | —H,<br>—C(=O)—CH=CH$_2$,<br>—(CH$_2$—CH$_2$—O)$_n$H,<br>—(CH$_2$—CH$_2$—(CH$_2$—O)$_n$H,<br>or<br>—(CH$_2$—CH$_2$—O)$_n$—(CH$_2$—CH$_2$—CH$_2$—O)$_n$H,<br>where each n is, independently, an integer from 1 to 18. | —H,<br>—C(=O)—CH=CH$_2$,<br>—(CH$_2$—CH$_2$—O)$_p$H,<br>—(CH$_2$—CH$_2$—(CH$_2$—O)$_p$H,<br>or<br>—(CH$_2$—CH$_2$—O)$_p$—(CH$_2$—CH$_2$—CH$_2$—O)$_p$H,<br>where each p is, independently, an integer from 1 to 18. |
| —CH(CCl$_3$)— | —C(=O)—CH=CH$_2$,<br>or<br>—(CH$_2$—CH$_2$—O)$_n$H,<br>where n is an integer from 1 to 18 | —C(=O)—CH=CH$_2$,<br>or<br>—(CH$_2$—CH$_2$—O)$_p$H,<br>where p is an integer from 1 to 18 |
| —CH(CCl$_3$)— | —H,<br>—C(=O)—CH=CH$_2$,<br>or<br>—(CH$_2$—CH$_2$—O)$_n$H,<br>where n is an integer from 1 to 18 | —H,<br>—C(=O)—CH=CH$_2$,<br>or<br>—(CH$_2$—CH$_2$—O)$_p$H,<br>where p is an integer from 1 to 18 |
| —CH(CCl$_3$)— | —H, or<br>—(CH$_2$—CH$_2$—O)$_n$H,<br>where n is an integer from 1 to 18 | —H, or<br>—(CH$_2$—CH$_2$—O)$_p$H,<br>where p is an integer from 1 to 18 |
| —CH(CCl$_3$)— | —H | —H |
| —CH(CCl$_3$)— | —H | —H |
| —CH(CCl$_3$)— | —H | —H |
| —CH(CCl$_3$)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —CH(CCl$_3$)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —CH(CCl$_3$)— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |
| —CH(CCl$_3$)— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |
| —CH(CCl$_3$)— | —C(=O)—CH=CH$_2$ | —C(=O)—CH=CH$_2$ |
| —CH(CCl$_3$)— | —(CH$_2$—CH$_2$—O)$_n$H,<br>where n is an integer from 1 to 18. | —(CH$_2$—CH$_2$—O)$_p$H,<br>where p is an integer from 1 to 18. |
| —CH(CCl$_3$)— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |

| $R_3$ | $R_4$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_q$H,<br>—(CH$_2$—CH$_2$—CH$_2$—O)$_q$H,<br>—N[CH$_2$—CH$_2$—O—C(=O)—CH=CH$_2$]$_2$, | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$, |

TABLE 7-continued

| | |
|---|---|
| —N[CH$_2$—CH$_2$—NH—C(=O)—CH=CH$_2$]$_2$, or<br>—NH—C(=O)—CH=CH2<br>where each q is, independently, an integer from 1 to 18. | —N[CH$_2$—CH$_2$—NH—C(=O)—CH=CH$_2$]$_2$, or<br>—NH—C(=O)—CH=CH$_2$<br>where each r is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each s is, independently, an integer from 1 to 18. | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each t is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ | —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ |

| | |
|---|---|
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

In some embodiments, compounds of formula II may have the following substitutions at each of, independently, X, $R_1$, $R_2$, $R_3$, $R_4$, $R_5$ and $R_6$, as shown in Table 8:

TABLE 8

| X | $R_1$ | $R_2$ |
|---|---|---|
| —C(Cl)$_2$— | —H,<br>—C(=O)—CH=CH$_2$,<br>—(CH$_2$—CH$_2$—O)$_n$H,<br>—(CH$_2$—CH$_2$—CH$_2$—O)$_n$H,<br>or<br>—(CH$_2$—CH$_2$—O)$_n$—(CH$_2$—CH$_2$—CH$_2$—O)$_n$H,<br>where each n is, independently, an integer from 1 to 18. | —H,<br>—C(=O)—CH=CH$_2$,<br>—(CH$_2$—CH$_2$—O)$_p$H,<br>—(CH$_2$—CH$_2$—CH$_2$—O)$_p$H,<br>or<br>—(CH$_2$—CH$_2$—O)$_p$—(CH$_2$—CH$_2$—CH$_2$—O)$_p$H,<br>where each p is, independently, an integer from 1 to 18. |
| —C(Cl)$_2$— | —C(=O)—CH=CH$_2$,<br>or<br>—(CH$_2$—CH$_2$—O)$_n$H,<br>where n is an integer from 1 to 18 | —C(=O)—CH=CH$_2$,<br>or<br>—(CH$_2$—CH$_2$—O)$_p$H,<br>where p is an integer from 1 to 18 |
| —C(Cl)$_2$— | —H,<br>—C(=O)—CH=CH$_2$,<br>or<br>—(CH$_2$—CH$_2$—O)$_n$H,<br>where n is an integer from 1 to 18 | —H,<br>—C(=O)—CH=CH$_2$,<br>or<br>—(CH$_2$—CH$_2$—O)$_p$H,<br>where p is an integer from 1 to 18 |
| —C(Cl)$_2$— | —H, or<br>—(CH$_2$—CH$_2$—O)$_n$H,<br>where n is an integer from 1 to 18 | —H, or<br>—(CH$_2$—CH$_2$—O)$_p$H,<br>where p is an integer from 1 to 18 |
| —C(Cl)$_2$— | —H | —H |
| —C(Cl)$_2$— | —H | —H |
| —C(Cl)$_2$— | —H | —H |
| —C(Cl)$_2$— | —(CH$_2$—CH$_2$—O)$_n$H,<br>where n is an integer from 1 to 18. | —(CH$_2$—CH$_2$—O)$_p$H,<br>where p is an integer from 1 to 18. |
| —C(Cl)$_2$— | —(CH$_2$—CH$_2$—O)$_n$H,<br>where n is an integer from 1 to 18. | —(CH$_2$—CH$_2$—O)$_p$H,<br>where p is an integer from 1 to 18. |
| —C(Cl)$_2$— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |
| —C(Cl)$_2$— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |
| —C(Cl)$_2$— | —C(=O)—CH=CH$_2$ | —C(=O)—CH=CH$_2$ |
| —C(Cl)$_2$— | —(CH$_2$—CH$_2$—O)$_n$H,<br>where n is an integer from 1 to 18. | —(CH$_2$—CH$_2$—O)$_p$H,<br>where p is an integer from 1 to 18. |
| —C(Cl)$_2$— | —(CH$_2$—CH$_2$—CH$_2$—O)$_n$H,<br>where n is an integer from 1 to 18 | —(CH$_2$—CH$_2$—CH$_2$—O)$_p$H,<br>where p is an integer from 1 to 18 |

| $R_3$ | $R_4$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_q$H,<br>—(CH$_2$—CH$_2$—CH$_2$—O)$_q$H,<br>—N[CH$_2$—CH$_2$—O—C(=O)—CH=CH$_2$]$_2$, | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$, |

TABLE 8-continued

| | |
|---|---|
| —N[CH$_2$—CH$_2$—NH—C(=O)—CH=CH$_2$]$_2$, or<br>—NH—C(=O)—CH=CH2<br>where each q is, independently, an integer from 1 to 18. | —N[CH$_2$—CH$_2$—NH—C(=O)—CH=CH$_2$]$_2$, or<br>—NH—C(=O)—CH=CH$_2$<br>where each r is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$ | —O—C(=O)—CH=CH$_2$<br>—N[CH$_2$O—C(=O)—CH=CH$_2$]$_2$<br>—N[CH$_2$O—C(=O)—CH=CH$_2$]$_2$ |
| —O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each s is, independently, an integer from 1 to 18. | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each t is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$ | —O—C(=O)—CH=CH$_2$<br>—N[CH$_2$O—C(=O)—CH=CH$_2$]$_2$<br>—N[CH$_2$O—C(=O)—CH=CH$_2$]$_2$ |
| —O—C(=O)—CH=CH$_2$<br>—N[CH$_2$O—C(=O)—CH=CH$_2$]$_2$ | —O—C(=O)—CH=CH$_2$<br>—N[CH$_2$O—C(=O)—CH=CH$_2$]$_2$ |

TABLE 8-continued

| | |
|---|---|
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

In some embodiments, compounds of formula II may have the following substitutions at each of, independently, X, $R_1$, $R_2$, $R_3$, $R_4$, $R_5$ and $R_6$, as shown in Table 9:

TABLE 9

| X | R$_1$ | R$_2$ |
|---|---|---|
| —O— | —H,<br>—C(=O)—CH=CH$_2$,<br>—(CH$_2$—CH$_2$—O)$_n$H,<br>—(CH$_2$—CH$_2$—CH$_2$—O)$_n$H,<br>or<br>—(CH$_2$—CH$_2$—O)$_n$—(CH$_2$—CH$_2$—CH$_2$—O)$_n$H,<br>where each n is,<br>independently,<br>an integer from<br>1 to 18. | —H,<br>—C(=O)—CH=CH$_2$,<br>—(CH$_2$—CH$_2$—O)$_p$H,<br>—(CH$_2$—CH$_2$—CH$_2$—O)$_p$H,<br>or<br>—(CH$_2$—CH$_2$—O)$_p$—(CH$_2$—CH$_2$—CH$_2$—O)$_p$H,<br>where each p is,<br>independently,<br>an integer from<br>1 to 18. |
| —O— | —C(=O)—CH=CH$_2$,<br>or<br>—(CH$_2$—CH$_2$—O)$_n$H,<br>where n is an<br>integer from 1 to<br>18 | —C(=O)—CH=CH$_2$,<br>or<br>—(CH$_2$—CH$_2$—O)$_p$H,<br>where p is an<br>integer from 1 to<br>18 |
| —O— | —H,<br>—C(=O)—CH=CH$_2$,<br>or<br>—(CH$_2$—CH$_2$—O)$_n$H,<br>where n is an<br>integer from 1 to<br>18 | —H,<br>—C(=O)—CH=CH$_2$,<br>or<br>—(CH$_2$—CH$_2$—O)$_p$H,<br>where p is an<br>integer from 1 to<br>18 |
| —O— | —H, or<br>—(CH$_2$—CH$_2$—O)$_n$H,<br>where n is an<br>integer from 1 to<br>18 | —H, or<br>—(CH$_2$—CH$_2$—O)$_p$H,<br>where p is an<br>integer from 1 to<br>18 |
| —O— | —H | —H |
| —O— | —H | —H |
| —O— | —H | —H |
| —O— | —(CH$_2$—CH$_2$—O)$_n$H,<br>where n is<br>an integer from<br>1 to 18. | —(CH$_2$—CH$_2$—O)$_p$H,<br>where p is<br>an integer from<br>1 to 18. |
| —O— | —(CH$_2$—CH$_2$—O)$_n$H,<br>where n is<br>an integer from<br>1 to 18. | —(CH$_2$—CH$_2$—O)$_p$H,<br>where p is<br>an integer from<br>1 to 18. |
| —O— | —(CH$_2$—CH$_2$—CH$_2$—O)$_n$H,<br>where n is an<br>integer from 1 to<br>18 | —(CH$_2$—CH$_2$—CH$_2$—O)$_p$H,<br>where p is an<br>integer from 1 to<br>18 |
| —O— | —(CH$_2$—CH$_2$—CH$_2$—O)$_n$H,<br>where n is an<br>integer from 1 to<br>18 | —(CH$_2$—CH$_2$—CH$_2$—O)$_p$H,<br>where p is an<br>integer from 1 to<br>18 |
| —O— | —C(=O)—CH=CH$_2$ | —C(=O)—CH=CH$_2$ |
| —O— | —(CH$_2$—CH$_2$—O)$_n$H,<br>where n is<br>an integer from<br>1 to 18. | —(CH$_2$—CH$_2$—O)$_p$H,<br>where p is<br>an integer from<br>1 to 18. |
| —O— | —(CH$_2$—CH$_2$—CH$_2$—O)$_n$H,<br>where n is an<br>integer from 1 to<br>18 | —(CH$_2$—CH$_2$—CH$_2$—O)$_p$H,<br>where p is an<br>integer from 1 to<br>18 |

| R$_3$ | R$_4$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_q$H,<br>—(CH$_2$—CH$_2$—CH$_2$—O)$_q$H,<br>—N[CH$_2$—CH$_2$—O—C(=O)—CH=CH$_2$]$_2$, | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$, |

TABLE 9-continued

| | |
|---|---|
| —N[CH$_2$—CH$_2$—NH—C(=O)—CH=CH$_2$]$_2$, or<br>—NH—C(=O)—CH=CH2<br>where each q is, independently, an integer from 1 to 18. | —N[CH$_2$—CH$_2$—NH—C(=O)—CH=CH$_2$]$_2$, or<br>—NH—C(=O)—CH=CH$_2$<br>where each r is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$ | —O—C(=O)CH=CH$_2$<br>—N[CH$_2$O—C(=O)—CH=CH$_2$]$_2$<br>—N[CH$_2$O—C(=O)—CH=CH$_2$]$_2$ |
| —O—C(=O)—CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ | —O—C(=O)CH=CH$_2$<br>—N[CH$_2$O—C(=O)—CH=CH$_2$]$_2$<br>—N(CH$_2$—CH$_2$—NH$_2$)$_2$<br>—N(CH$_2$—CH$_2$—NH$_2$)$_2$ |

| R$_5$ | R$_6$ |
|---|---|
| —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_s$H,<br>—(CH$_2$—CH$_2$—CH$_2$—O)$_s$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each s is, independently, an integer from 1 to 18. | —N(CH$_2$—CH$_2$—NH$_2$)$_2$,<br>—O—C(=O)—CH=CH$_2$,<br>—N[CH$_2$O—C(=O)—CH=CH$_2$]$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$, or<br>—N[CH$_2$—CH$_2$—NH—C(=O)—CH=CH$_2$]$_2$, or<br>—NH—C(=O)—CH=CH$_2$<br>where each t is, independently, an integer from 1 to 18. |
| —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ | —O—C(=O)—CH=CH$_2$,<br>—N[CH$_2$O—C(=O)—CH=CH$_2$]$_2$,<br>—N[CH$_2$—CH$_2$—O—C(=O)—CH=CH$_2$]$_2$, or<br>—NH—C(=O)—CH=CH$_2$ |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$, or<br>—N(CH$_2$—CH$_2$—NH$_2$)$_2$. | —O—C(=O)—CH=CH$_2$, or<br>—N(CH$_2$—CH$_2$—NH$_2$)$_2$. |
| —O—C(=O)—CH=CH$_2$<br>—N[CH$_2$O—C(=O)—CH=CH$_2$]$_2$<br>—N(CH$_2$—CH$_2$—NH$_2$)$_2$ | —O—C(=O)—CH=CH$_2$<br>—N[CH$_2$O—C(=O)—CH=CH$_2$]$_2$<br>—N(CH$_2$—CH$_2$—NH$_2$)$_2$ |
| —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ | —O—C(=O)—CH=CH$_2$<br>—N[CH$_2$O—C(=O)—CH=CH$_2$]$_2$<br>—N[CH$_2$O—C(=O)—CH=CH$_2$]$_2$<br>—O—C(=O)—CH=CH$_2$<br>—N[CH$_2$O—C(=O)—CH=CH$_2$]$_2$ |

TABLE 9-continued

| | |
|---|---|
| —N(CH$_2$—CH$_2$—NH$_2$)$_2$ | —N(CH$_2$—CH$_2$—NH$_2$)$_2$ |
| —N(CH$_2$—CH$_2$—NH$_2$)$_2$ | —N(CH$_2$—CH$_2$—NH$_2$)$_2$ |

In some embodiments, compounds of formula II may have the following substitutions at each of, independently, X, R$_1$, R$_2$, R$_3$, R$_4$, R$_5$ and R$_6$, as shown in Table 10:

TABLE 10

| X | R$_1$ | R$_2$ |
|---|---|---|
| —C(F)$_2$— | —H, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH$_2$—CH$_2$—O)$_n$H, where each n is, independently, an integer from 1 to 18. | —H, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH$_2$—CH$_2$—O)$_p$H, where each p is, independently, an integer from 1 to 18. |
| —C(F)$_2$— | —C(=O)—CH=CH$_2$, or —(CH$_2$—CH$_2$—O)$_n$H, where n is an integer from 1 to 18 | —C(=O)—CH=CH$_2$, or —(CH$_2$—CH$_2$—O)$_p$H, where p is an integer from 1 to 18 |
| —C(F)$_2$— | —H, —C(=O)—CH=CH$_2$, or —(CH$_2$—CH$_2$—O)$_n$H, where n is an integer from 1 to 18 | —H, C(=O) CH=CH$_2$, or —(CH$_2$—CH$_2$—O)$_p$H, where p is an integer from 1 to 18 |
| —C(F)$_2$— | —H, or —(CH$_2$—CH$_2$—O)$_n$H, where n is an integer from 1 to 18 | —H, or —(CH$_2$—CH$_2$—O)$_p$H, where p is an integer from 1 to 18 |
| —C(F)$_2$— | —H | —H |
| —C(F)$_2$— | —H | —H |
| —C(F)$_2$— | —H | —H |
| —C(F)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(F)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(F)$_2$— | —(CH$_2$—CH$_2$—CH$_2$—O)$_n$H, where n is an integer from 1 to 18 | —(CH$_2$—CH$_2$—CH$_2$—O)$_p$H, where p is an integer from 1 to 18 |
| —C(F)$_2$— | —(CH$_2$—CH$_2$—CH$_2$—O)$_n$H, where n is an integer from 1 to 18 | —(CH$_2$—CH$_2$—CH$_2$—O)$_p$H, where p is an integer from 1 to 18 |
| —C(F)$_2$— | —C(=O)—CH=CH$_2$ | —C(=O)—CH=CH$_2$ |
| —C(F)$_2$— | —(CH$_2$—CH$_2$—O)$_n$H, where n is an integer from 1 to 18. | —(CH$_2$—CH$_2$—O)$_p$H, where p is an integer from 1 to 18. |
| —C(F)$_2$— | —(CH$_2$—CH$_2$—CH$_2$—O)$_n$H, where n is an integer from 1 to 18 | —(CH$_2$—CH$_2$—CH$_2$—O)$_p$H, where p is an integer from 1 to 18 |

| R$_3$ | R$_4$ |
|---|---|
| —N(CH$_2$—CH$_2$—NH$_2$)$_2$, —O—C(=O)—CH=CH$_2$, | —N(CH$_2$—CH$_2$—NH$_2$)$_2$, —O—C(=O)—CH=CH$_2$, |

TABLE 10-continued

| | |
|---|---|
| —N[CH₂O—C(=O)—CH=CH₂]₂, | —N[CH₂O—C(=O)—CH=CH₂]₂, |
| —(CH₂—CH₂—O)$_q$H, | —(CH₂—CH₂—O)$_r$H, |
| —(CH₂—CH₂—CH₂—O)$_q$H, | —(CH₂—CH₂—CH₂—O)$_r$H, |
| —N[CH₂—CH₂—O—C(=O)—CH=CH₂]₂, | —N[CH₂—CH₂—O—C(=O)—CH=CH₂]₂, |
| —N[CH₂—CH₂—NH—C(=O)—CH=CH₂]₂, | —N[CH₂—CH₂—NH—C(=O)—CH=CH₂]₂, |
| or | or |
| —NH—C(=O)—CH=CH2 | —NH—C(=O)—CH=CH₂ |
| where each q is, independently, an integer from 1 to 18. | where each r is, independently, an integer from 1 to 18. |
| —O—C(=O)—CH=CH₂, | —O—C(=O)—CH=CH₂, |
| —N[CH₂O—C(=O)—CH=CH₂]₂, | —N[CH₂O—C(=O)—CH=CH₂]₂, |
| —N[CH₂—CH₂—O—C(=O)—CH=CH₂]₂, | —N[CH₂—CH₂—O—C(=O)—CH=CH₂]₂, |
| or | or |
| —NH—C(=O)—CH=CH₂ | —NH—C(=O)—CH=CH₂ |
| —O—C(=O)—CH=CH₂, | —O—C(=O)—CH=CH₂, |
| or | or |
| —N(CH₂—CH₂—NH₂)₂. | —N(CH₂—CH₂—NH₂)₂. |
| —O—C(=O)—CH=CH₂, | —O—C(=O)—CH=CH₂, |
| or | or |
| —N(CH₂—CH₂—NH₂)₂. | —N(CH₂—CH₂—NH₂)₂. |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N(CH₂—CH₂—NH₂)₂ | —N(CH₂—CH₂—NH₂)₂ |
| —O—C(=O)—CH=CH₂ | —O—C(=O)CH=CH₂ |
| —N[CH₂O—C(=O)—CH=CH₂]₂ | —N[CH₂O—C(=O)—CH=CH₂]₂ |
| —N[CH₂O—C(=O)—CH=CH₂]₂ | —N[CH₂O—C(=O)—CH=CH₂]₂ |
| —O—C(=O)—CH=CH₂ | —O—C(=O)CH=CH₂ |
| —N[CH₂O—C(=O)—CH=CH₂]₂ | —N[CH₂O—C(=O)—CH=CH₂]₂ |
| —N(CH₂—CH₂—NH₂)₂ | —N(CH₂—CH₂—NH₂)₂ |
| —N(CH₂—CH₂—NH₂)₂ | —N(CH₂—CH₂—NH₂)₂ |

| R₅ | R₆ |
|---|---|
| —N(CH₂—CH₂—NH₂)₂, | —N(CH₂—CH₂—NH₂)₂, |
| —O—C(=O)—CH=CH₂, | —O—C(=O)—CH=CH₂, |
| —N[CH₂O—C(=O)—CH=CH₂]₂, | —N[CH₂O—C(=O)—CH=CH₂]₂, |
| —(CH₂—CH₂—O)$_s$H, | —(CH₂—CH₂—O)$_t$H, |
| —(CH₂—CH₂—CH₂—O)$_s$H, | —(CH₂—CH₂—CH₂—O)$_t$H, |
| —N[CH₂—CH₂—O—C(=O)—CH=CH₂]₂, | —N[CH₂—CH₂—O—C(=O)—CH=CH₂]₂, |
| or | or |
| —N[CH₂—CH₂—NH—C(=O)—CH=CH₂]₂, | —N[CH₂—CH₂—NH—C(=O)—CH=CH₂]₂, |
| or | or |
| —NH—C(=O)—CH=CH₂ | —NH—C(=O)—CH=CH₂ |
| where each s is, independently, an integer from 1 to 18. | where each t is, independently, an integer from 1 to 18. |
| —O—C(=O)—CH=CH₂, | —O—C(=O)—CH=CH₂, |
| —N[CH₂O—C(=O)—CH=CH₂]₂, | —N[CH₂O—C(=O)—CH=CH₂]₂, |
| —N[CH₂—CH₂—O—C(=O)—CH=CH₂]₂, | —N[CH₂—CH₂—O—C(=O)—CH=CH₂]₂, |
| or | or |
| —NH—C(=O)—CH=CH₂ | —NH—C(=O)—CH=CH₂ |
| —O—C(=O)—CH=CH₂, | —O—C(=O)—CH=CH₂, |
| or | or |
| —N(CH₂—CH₂—NH₂)₂. | —N(CH₂—CH₂—NH₂)₂. |
| —O—C(=O)—CH=CH₂, | —O—C(=O)—CH=CH₂, |
| or | or |
| —N(CH₂—CH₂—NH₂)₂. | —N(CH₂—CH₂—NH₂)₂. |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N(CH₂—CH₂—NH₂)₂ | —N(CH₂—CH₂—NH₂)₂ |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |
| —N[CH₂O—C(=O)—CH=CH₂]₂ | —N[CH₂O—C(=O)—CH=CH₂]₂ |
| —O—C(=O)—CH=CH₂ | —O—C(=O)—CH=CH₂ |
| —N[CH₂O—C(=O)—CH=CH₂]₂ | —N[CH₂O—C(=O)—CH=CH₂]₂ |

TABLE 10-continued
| —N(CH₂—CH₂—NH₂)₂ | —N(CH₂—CH₂—NH₂)₂ |
| —N(CH₂—CH₂—NH₂)₂ | —N(CH₂—CH₂—NH₂)₂ |
Non-limiting examples of compounds represented by formula II include, but are not limited to, the following compounds:
9
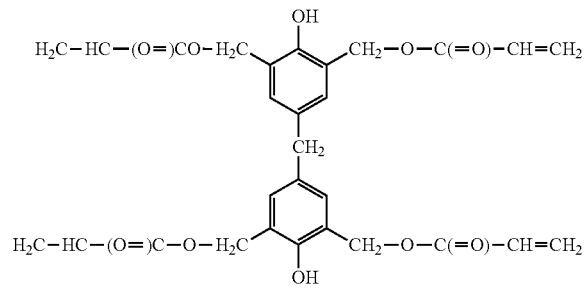
10
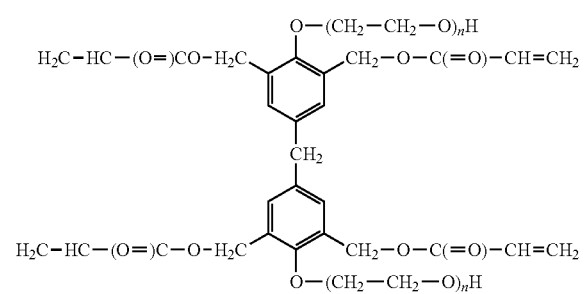
11
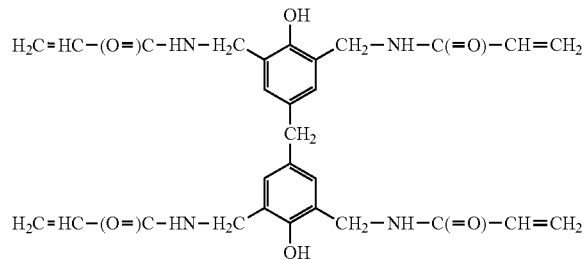
12
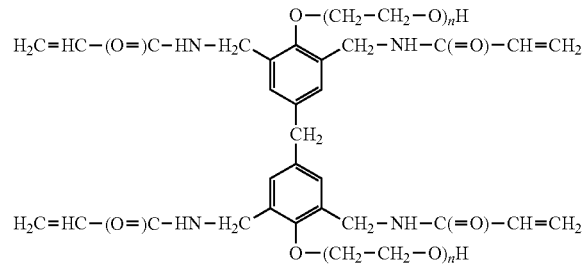
13
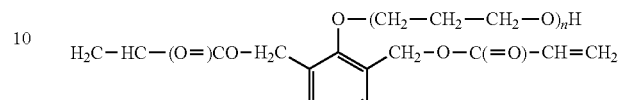
14
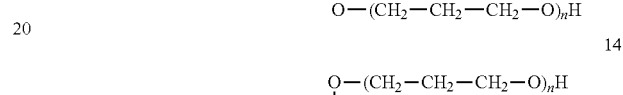
15
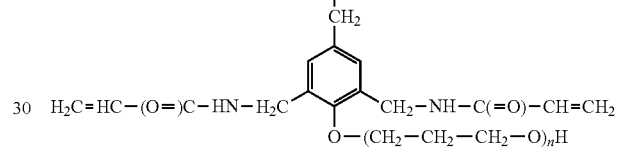
16
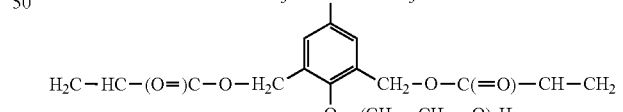
17
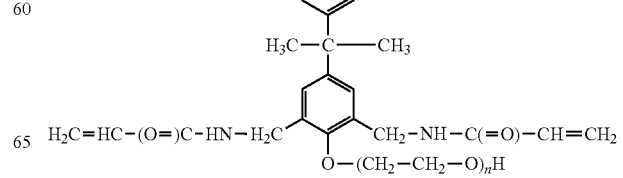

18

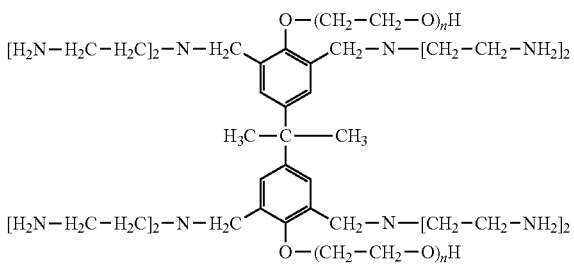

19

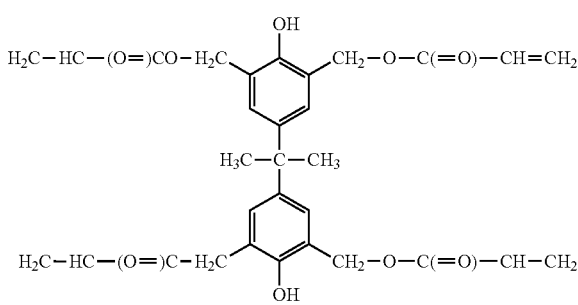

In some embodiments, a compound may be of formula III

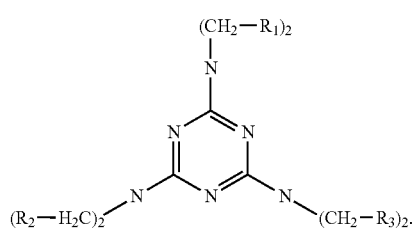

In some embodiments, each $R_1$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_n$H, —(CH$_2$—CH$_2$—CH$_2$—O)$_n$H, —N[CH$_2$—CH$_2$—O—C(=O)—CH=CH$_2$]$_2$, —N[CH$_2$O—C(=O)—CH=CH$_2$]$_2$, —N[CH$_2$—CH$_2$—NH—C(=O)—CH=CH$_2$]$_2$, —NH—C(=O)CH=CH$_2$, or block copolymers of —(CH$_2$—CH$_2$—O)$_n$—(CH$_2$—CH$_2$—CH$_2$—O)$_n$H, where each n is, independently, an integer from 1 to 18. In some embodiments, each $R_1$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_n$H, —(CH$_2$—CH$_2$—CH$_2$—O)$_n$H, or —N[CH$_2$—CH$_2$—O—C(=O)—CH=CH$_2$]$_2$. In some embodiments, each $R_1$ may be —H, —OH, —NH$_2$, —N(CH$_2$—CH$_2$—OH)$_2$, —N(CH$_2$—CH$_2$—NH$_2$)$_2$, or —O—C(=O)—CH=CH$_2$.

In some embodiments, each $R_2$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, —N[CH$_2$O—C(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, or —NH—C(=O)CH=CH$_2$, or block copolymers of —(CH$_2$—CH$_2$—O)$_p$—(CH$_2$—CH$_2$—CH$_2$—O)$_p$H, where each p is, independently, an integer from 1 to 18. In some embodiments, each $R_2$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, or —N[CH$_2$O—C(=O)—CH=CH$_2$]$_2$. In some embodiments, each $R_2$ may be —H, —OH, —NH$_2$, —N(CH$_2$—CH$_2$—OH)$_2$, —N(CH$_2$—CH$_2$—NH$_2$)$_2$, or —O—C(=O)—CH=CH$_2$.

In some embodiments, each $R_3$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, —N[CH2O—C(=O)—CH=CH$_2$]$_2$, —N[CH$_2$—CH$_2$—O—C(=O)—CH=CH$_2$]$_2$, —N[CH$_2$—CH$_2$—NH—C(=O)—CH=CH$_2$]$_2$, —NH—C(=O)CH=CH$_2$ or block copolymers of —(CH$_2$—CH$_2$—O)$_q$—(CH$_2$—CH$_2$—CH$_2$—O)$_q$H, where each q is, independently, an integer from 1 to 18. In some embodiments, each $R_3$ may be —H, —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, or —N[CH$_2$O—C(=O)—CH=CH$_2$]$_2$. In some embodiments, each $R_3$ may be —H, —OH, —NH$_2$, —N(CH$_2$—CH$_2$—OH)$_2$, —N(CH$_2$—CH$_2$—NH$_2$)$_2$, or —O—C(=O)—CH=CH$_2$.

In some embodiments, compounds of formula III may have the following substitutions at each of, independently, $R_1$, $R_2$ and $R_3$, as shown in Table 11:

TABLE 11

| $R_1$ | $R_2$ | $R_3$ |
|---|---|---|
| —H, | —H, | —H, |
| —OH, | —OH, | —OH, |
| —NH$_2$, | —NH$_2$, | —NH$_2$, |
| —N(CH$_2$—CH$_2$—OH)$_2$, | —N(CH$_2$—CH$_2$—OH)$_2$, | —N(CH$_2$—CH$_2$—OH)$_2$, |
| —N(CH$_2$—CH$_2$—NH$_2$)$_2$, | —N(CH$_2$—CH$_2$—NH$_2$)$_2$, | —N(CH$_2$—CH$_2$—NH$_2$)$_2$, |
| —O—C(=O)—CH=CH$_2$, | —O—C(=O)—CH=CH$_2$, | —O—C(=O)—CH=CH$_2$, |
| —(CH$_2$—CH$_2$—O)$_n$H, | —(CH$_2$—CH$_2$—O)$_p$H, | —(CH$_2$—CH$_2$—O)$_q$H, |
| —(CH$_2$—CH$_2$—CH$_2$—O)$_n$H, | —(CH$_2$—CH$_2$—CH$_2$—O)$_p$H, | —(CH$_2$—CH$_2$—CH$_2$—O)$_q$H, |
| —N[CH$_2$—CH$_2$—O—C(=O)—CH=CH$_2$]$_2$, | —N[CH$_2$OC(=O)—CH=CH$_2$]$_2$, | —N[CH$_2$O—C(=O)—CH=CH$_2$]$_2$, |
| —N[CH$_2$O—C(=O)—CH=CH$_2$]$_2$, | —N[CH$_2$—CH$_2$—O—C(=O)—CH=CH$_2$]$_2$, | —N[CH$_2$—CH$_2$—O—C(=O)—CH=CH$_2$]$_2$, |
| —N[CH$_2$—CH$_2$—NH—C(=O)—CH=CH$_2$]$_2$, | —(CH$_2$—CH$_2$—O)$_p$—(CH$_2$—CH$_2$—CH$_2$—O)$_p$H, | —(CH$_2$—CH$_2$—O)$_q$—(CH$_2$—CH$_2$—CH$_2$—O)$_q$H, |
| —(CH$_2$—CH$_2$—O)$_n$—(CH$_2$—CH$_2$—CH$_2$—O)$_n$H, or | —N[CH$_2$—CH$_2$—NH—C(=O)—CH=CH$_2$]$_2$, or | —N[CH$_2$—CH$_2$—NH—C(=O)—CH=CH$_2$]$_2$, or |
| —NH—C(=O)CH=CH$_2$ | —NH—C(=O)CH=CH$_2$ | —NH—C(=O)CH=CH$_2$ |
| where each n is, independently, an integer from 1 to 18. | where each p is, independently, an integer from 1 to 18. | where each q is, independently, an integer from 1 to 18. |

TABLE 11-continued

| R₁ | R₂ | R₃ |
|---|---|---|
| —H, | —H, | —H, |
| —OH, | —OH, | —OH, |
| —NH₂, | —NH₂, | —NH₂, |
| —N(CH₂—CH₂—OH)₂, | —N(CH₂—CH₂—OH)₂, | —N(CH₂—CH₂—OH)₂, |
| —N(CH₂—CH₂—NH₂)₂, | —N(CH₂—CH₂—NH₂)₂, | —N(CH₂—CH₂—NH₂)₂, |
| —N[CH₂O—C(=O)—CH=CH₂]₂, or | —N[CH₂O—C(=O)—CH=CH₂]₂, or | —N[CH₂O—C(=O)—CH=CH₂]₂, or |
| —O—C(=O)—CH=CH₂. | —O—C(=O)—CH=CH₂. | —O—C(=O)—CH=CH₂. |
| —N[CH₂—CH₂—O—C(=O)—CH=CH₂]₂ or | —N[CH₂—CH₂—O—C(=O)—CH=CH₂]₂ or | —N[CH₂—CH₂—O—C(=O)—CH=CH₂]₂ or |
| —N[CH₂O—C(=O)—CH=CH₂]₂ | —N[CH₂O—C(=O)—CH=CH₂]₂ | —N[CH₂O—C(=O)—CH=CH₂]₂ |
| —N(CH₂—CH₂—OH)₂ | —N(CH₂—CH₂—OH)₂ | —N(CH₂—CH₂—OH)₂ |
| —N(CH₂—CH₂—NH₂)₂ | —N(CH₂—CH₂—NH₂)₂ | —N(CH₂—CH₂—NH₂)₂ |
| —NH₂ | —NH₂ | —NH₂ |
| —O—C(=O)—CH=CH₂ | —O—C(=O)—CH=CH₂ | —O—C(=O)—CH=CH₂ |
| —N[CH₂—CH₂—O—C(=O)—CH=CH₂]₂ | —N[CH₂—CH₂—O—C(=O)—CH=CH₂]₂ | —N[CH₂—CH₂—O—C(=O)—CH=CH₂]₂ |
| —N[CH₂O—C(=O)—CH=CH₂]₂ | —N[CH₂O—C(=O)—CH=CH₂]₂ | —N[CH₂O—C(=O)—CH=CH₂]₂ |
| —N[CH₂—CH₂—NH—C(=O)—CH=CH₂]₂ | —N[CH₂—CH₂—NH—C(=O)—CH=CH₂]₂ | —N[CH₂—CH₂—NH—C(=O)—CH=CH₂]₂ |

Non-limiting examples of compounds represented by formula III include, but are not limited to, the following compounds:

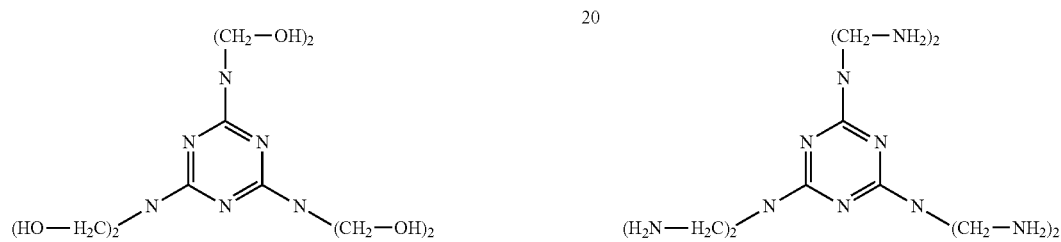

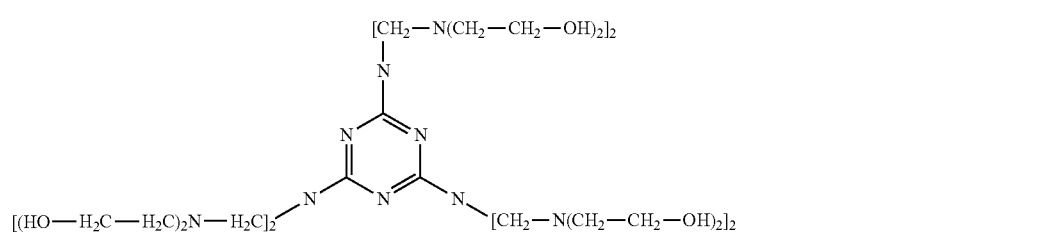

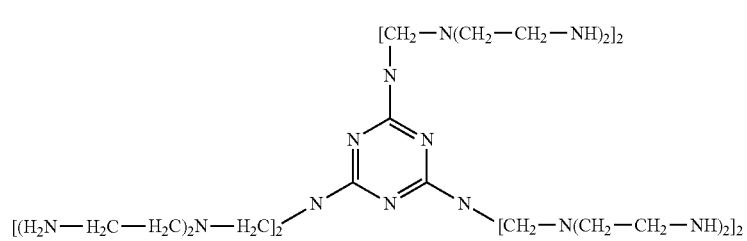

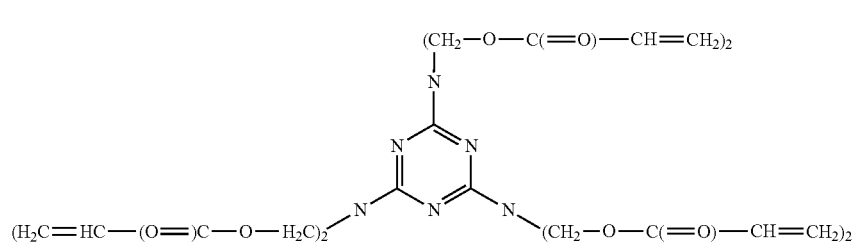

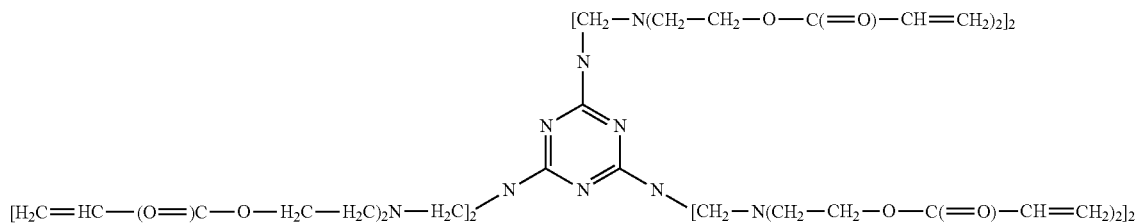

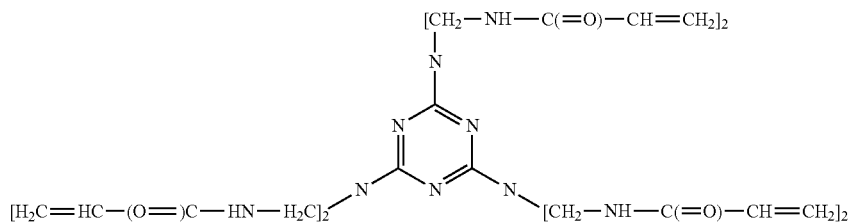

In some embodiments, a compound may be of formula IV

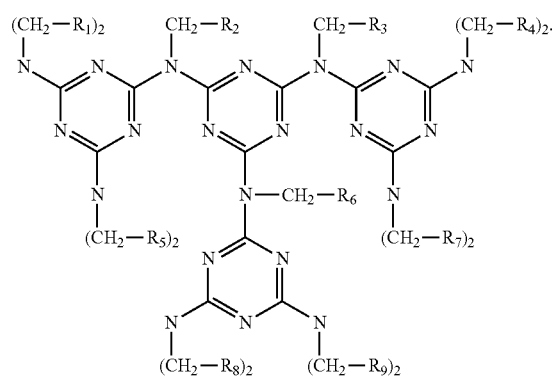

In some embodiments, each $R_1$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$O)$_n$H, —(CH$_2$—CH$_2$—CH$_2$—O)$_n$H, —N[CH$_2$O—C(=O)—CH=CH$_2$]$_2$, —N[CH$_2$—CH$_2$—O—C(=O)—CH=CH$_2$]$_2$, —NH—C(=O)CH=CH$_2$, or —N[CH$_2$—CH$_2$—NH—C(=O)—CH=CH$_2$]$_2$, where each n is, independently, an integer from 1 to 18. In some embodiments, each $R_1$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_n$H, —(CH$_2$—CH$_2$—CH$_2$—O)$_n$H, or —N[CH$_2$O—C(=O)—CH=CH$_2$]$_2$. In some embodiments, each $R_1$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_n$H. In some embodiments, each $R_1$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, or —O—C(=O)—CH=CH$_2$.

In some embodiments, $R_2$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, —N[CH$_2$O—C(=O)—CH=CH$_2$]$_2$, —N[CH$_2$—CH$_2$—O—C(=O)—CH=CH$_2$]$_2$, —NH—C(=O)CH=CH$_2$, or —N[CH$_2$—CH$_2$—NH—C(=O)—CH=CH$_2$]$_2$, where p is an integer from 1 to 18. In some embodiments, $R_2$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_p$H, —(CH$_2$—CH$_2$—CH$_2$—O)$_p$H, or —N[CH$_2$O—C(=O)—CH=CH$_2$]$_2$. In some embodiments, $R_2$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_p$H. In some embodiments, each $R_2$ may be —N(CH$_2$—CH$_2$—OH)$_2$, —N(CH$_2$—CH$_2$—NH$_2$)$_2$, —N[CH2O—C(=O)—CH=CH$_2$]$_2$, or —O—C(=O)—CH=CH$_2$.

In some embodiments, $R_3$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, —N[CH$_2$O—C(=O)—CH=CH$_2$]$_2$, —N[CH$_2$—CH$_2$—O—C(=O)—CH=CH$_2$]$_2$, —NH—C(=O)CH=CH$_2$, or —N[CH$_2$—CH$_2$—NH—C(=O)—CH=CH$_2$]$_2$, where q is an integer from 1 to 18. In some embodiments, $R_3$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_q$H, —(CH$_2$—CH$_2$—CH$_2$—O)$_q$H, or —N[CH$_2$O—C(=O)—CH=CH$_2$]$_2$. In some embodiments, $R_3$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_q$H. In some embodiments, each $R_3$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$, or —O—C(=O)—CH=CH$_2$.

In some embodiments, each $R_4$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_r$H, —(CH$_2$—CH$_2$—CH$_2$—O)$_r$H, —N[CH$_2$O C(=O)—CH=CH$_2$]$_2$, —NH—C(=O)CH=CH$_2$, —N[CH$_2$—CH$_2$—O—C(=O)—CH=CH$_2$]$_2$, or —N[CH$_2$—CH$_2$—

NH—C(=O)—CH=CH$_2$]$_2$, where each r is, independently, an integer from 1 to 18. In some embodiments, each R$_4$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_r$H, —(CH$_2$—CH$_2$—CH$_2$—O)$_r$H, or —N[CH$_2$O—C(=O)—CH=CH$_2$]$_2$. In some embodiments, each R$_4$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_r$H. In some embodiments, each R$_4$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NHC(=O)CH=CH$_2$, or —O—C(=O)—CH=CH$_2$.

In some embodiments, each R$_5$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_t$H, —(CH$_2$—CH$_2$—CH$_2$—O)$_t$H, —N[CH$_2$O—C(=O)—CH=CH$_2$]$_2$, —N[CH$_2$—CH$_2$—O—C(=O)—CH=CH$_2$]$_2$, —NH—C(=O)CH=CH$_2$, or —N[CH$_2$—CH$_2$—NH—C(=O)—CH=CH$_2$]$_2$, where each t is, independently, an integer from 1 to 18. In some embodiments, each R$_5$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_t$H, —(CH$_2$—CH$_2$—CH$_2$—O)$_t$H, or —N[CH$_2$O—C(=O)—CH=CH$_2$]$_2$. In some embodiments, each R$_5$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_t$H. In some embodiments, each R$_5$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$, or —O—C(=O)—CH=CH$_2$.

In some embodiments, R$_6$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_v$H, —(CH$_2$—CH$_2$—CH$_2$—O)$_v$H, —N[CH$_2$O—C(=O)—CH=CH$_2$]$_2$, —NH—C(=O)CH=CH$_2$, —N[CH$_2$—CH$_2$—O—C(=O)—CH=CH$_2$]$_2$, or —N[CH$_2$—CH$_2$—NH—C(=O)—CH=CH$_2$]$_2$, where v is an integer from 1 to 18. In some embodiments, R$_6$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_v$H, —(CH$_2$—CH$_2$—CH$_2$—O)$_v$H, or —N[CH$_2$O—C(=O)—CH=CH$_2$]$_2$. In some embodiments, R$_6$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_v$H. In some embodiments, each R$_6$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$, or —O—C(=O)—CH=CH$_2$.

In some embodiments, each R$_7$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_w$H, —(CH$_2$—CH$_2$—CH$_2$—O)$_w$H, —N[CH$_2$O—C(=O)—CH=CH$_2$]$_2$, —NH—C(=O)CH=CH$_2$, —N[CH$_2$—CH$_2$—O—C(=O)—CH=CH$_2$]$_2$, or —N[CH$_2$—CH$_2$—NH—C(=O)—CH=CH$_2$]$_2$, where each w is, independently, an integer from 1 to 18. In some embodiments, each R$_7$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_w$H, —(CH$_2$—CH$_2$—CH$_2$—O)$_w$H, or —N[CH$_2$O—C(=O)—CH=CH$_2$]$_2$. In some embodiments, each R$_7$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_w$H. In some embodiments, each R$_7$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$, or —O—C(=O)—CH=CH$_2$.

In some embodiments, each R$_8$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_y$H, —(CH$_2$—CH$_2$—CH$_2$—O)$_y$H, —N[CH$_2$O—C(=O)—CH=CH$_2$]$_2$, —NH—C(=O)CH=CH$_2$, —N[CH$_2$—CH$_2$—O—C(=O)—CH=CH$_2$]$_2$, or —N[CH$_2$—CH$_2$—NH—C(=O)—CH=CH$_2$]$_2$, where each y is, independently, an integer from 1 to 18. In some embodiments, each R$_8$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_y$H, —(CH$_2$—CH$_2$—CH$_2$—O)$_y$H, or —N[CH$_2$O—C(=O)—CH=CH$_2$]$_2$. In some embodiments, each R$_8$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_y$H. In some embodiments, each R$_8$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$, or —O—C(=O)—CH=CH$_2$.

In some embodiments, each R$_9$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_z$H, —(CH$_2$—CH$_2$—CH$_2$—O)$_z$H, —N[CH$_2$O—C(=O)—CH=CH$_2$]$_2$, —NH—C(=O)CH=CH$_2$, —N[CH$_2$—CH$_2$—O—C(=O)—CH=CH$_2$]$_2$, or —N[CH$_2$—CH$_2$—NH—C(=O)—CH=CH$_2$]$_2$, where each z is, independently, an integer from 1 to 18. In some embodiments, each R$_9$ may be —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_z$H, —(CH$_2$—CH$_2$—CH$_2$—O)$_z$H, or —N[CH$_2$O—C(=O)—CH=CH$_2$]$_2$. In some embodiments, each R$_9$ may be —OH, —NH$_2$, —N(CH$_2$—CH$_2$—OH)$_2$, —N(CH$_2$—CH$_2$—NH$_2$)$_2$, —O—C(=O)—CH=CH$_2$, or —(CH$_2$—CH$_2$—O)$_z$H. In some embodiments, each R$_9$ may be —N(CH$_2$—CH$_2$—OH)$_2$, —N(CH$_2$—CH$_2$—NH$_2$)$_2$, —N[CH$_2$O—C(=O)—CH=CH$_2$]$_2$, —NH—C(=O)CH=CH$_2$ or —O—C(=O)—CH=CH$_2$.

In some embodiments, compounds of formula IV may have the following substitutions at each of, independently, R$_1$, R$_2$, R$_3$, R$_4$, R$_5$, R$_6$, R$_7$, R$_8$, and R$_9$ as shown in Table 12:

TABLE 12

| R$_1$ | R$_2$ | R$_3$ |
|---|---|---|
| —OH, | —OH, | —OH, |
| —NH$_2$, | —NH$_2$, | —NH$_2$, |
| —N(CH$_2$—CH$_2$—OH)$_2$, | —N(CH$_2$—CH$_2$—OH)$_2$, | —N(CH$_2$—CH$_2$—OH)$_2$, |
| —N(CH$_2$—CH$_2$—NH$_2$)$_2$, | —N(CH$_2$—CH$_2$—NH$_2$)$_2$, | —N(CH$_2$—CH$_2$—NH$_2$)$_2$, |
| —O—C(=O)—CH=CH$_2$, | —O—C(=O)—CH=CH$_2$, | —O—C(=O)—CH=CH$_2$, |
| —(CH$_2$—CH$_2$—O)$_n$H, | —(CH$_2$—CH$_2$—O)$_p$H, | —(CH$_2$—CH$_2$—O)$_q$H, |
| —(CH$_2$—CH$_2$—CH$_2$—O)$_n$H, | —(CH$_2$—CH$_2$—CH$_2$—O)$_p$H, | —(CH$_2$—CH$_2$—CH$_2$—O)$_q$H, |

TABLE 12-continued

| | | |
|---|---|---|
| —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, where each n is, independently, an integer from 1 to 18. | —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, where each p is, independently, an integer from 1 to 18. | —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, NHC(=O)CH=CH2 where each q is, independently, an integer from 1 to 18. |
| —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH —NH$_2$ —N(CH$_2$—CH$_2$—OH)$_2$ —N(CH$_2$—CH$_2$—NH$_2$)$_2$ —O—C(=O)—CH=CH$_2$ —N[CH$_2$O—C(=O)CH=CH$_2$]$_2$, —N[CH$_2$—CH$_2$O—C(=O)—CH=CH$_2$]$_2$ —N[CH$_2$—CH$_2$—NH—C(=O)—CH=CH$_2$]$_2$ | —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH —NH$_2$ —N(CH$_2$—CH$_2$—OH)$_2$ —N(CH$_2$—CH$_2$—NH$_2$)$_2$ —O—C(=O)—CH=CH$_2$ —N[CH$_2$O—C(=O)CH=CH$_2$]$_2$, —N[CH$_2$—CH$_2$O—C(=O)—CH=CH$_2$]$_2$ —N[CH$_2$—CH$_2$—NH—C(=O)—CH=CH$_2$]$_2$ | —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH —NH$_2$ —N(CH$_2$—CH$_2$—OH)$_2$ —N(CH$_2$—CH$_2$—NH$_2$)$_2$ —O—C(=O)—CH=CH$_2$ —N[CH$_2$O—C(=O)CH=CH$_2$]$_2$, —N[CH$_2$—CH$_2$O—C(=O)—CH=CH$_2$]$_2$ —N[CH$_2$—CH$_2$—NH—C(=O)—CH=CH$_2$]$_2$ |
| $R_4$ | $R_5$ | $R_6$ |
| —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_r$H, —(CH$_2$—CH$_2$—CH$_2$—O)$_r$H, —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, NHC(=O)CH=CH2 where each r is, independently, an integer from 1 to 18. —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH | —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_t$H, —(CH$_2$—CH$_2$—CH$_2$—O)$_t$H, —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, NHC(=O)CH=CH2 where each t is, independently, an integer from 1 to 18. —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH | —OH, —NH$_2$, —N(CH$_2$—CH$_2$—OH)$_2$, —N(CH$_2$—CH$_2$—NH$_2$)$_2$, —O—C(=O)—CH=CH$_2$, —(CH$_2$—CH$_2$—O)$_v$H, —(CH$_2$—CH$_2$—CH$_2$—O)$_v$H, —N[CH$_2$O—C(=O)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$, NHC(=O)CH=CH2 where each v is, independently, an integer from 1 to 18. —N(CH$_2$—CH$_2$—OH)$_2$, —N(CH$_2$—CH$_2$—NH$_2$)$_2$, —O—C(=O)—CH=CH$_2$, —N[CH$_2$O—C(=0)CH=CH$_2$]$_2$, —N[CH$_2$—CH$_2$—O—C(=O)—CH=CH$_2$]$_2$, or —N[CH$_2$—CH$_2$—NH—C(=O)—CH=CH$_2$]$_2$. —N(CH$_2$—CH$_2$—OH)$_2$, —N(CH$_2$—CH$_2$—NH$_2$)$_2$, —N[CH$_2$O—C(=O)CH=CH$_2$]$_2$, or —O—C(=O)—CH=CH$_2$. —N(CH$_2$—CH$_2$—OH)$_2$ —OH |

TABLE 12-continued

| | | |
|---|---|---|
| —NH$_2$ | —NH$_2$ | —NH$_2$ |
| —N(CH$_2$—CH$_2$—OH)$_2$ | —N(CH$_2$—CH$_2$—OH)$_2$ | —N(CH$_2$—CH$_2$—OH)$_2$ |
| —N(CH$_2$—CH$_2$—NH$_2$)$_2$ | —N(CH$_2$—CH$_2$—NH$_2$)$_2$ | —N(CH$_2$—CH$_2$—NH$_2$)$_2$ |
| —O—C(=O)—CH=CH$_2$ | —O—C(=O)—CH=CH$_2$ | —O—C(=O)—CH=CH$_2$ |
| —N[CH$_2$O—C(=O)CH=CH$_2$]$_2$, | —N[CH$_2$O—C(=O)CH=CH$_2$]$_2$, | —N[CH$_2$O—C(=O)CH=CH$_2$]$_2$, |
| —N[CH$_2$—CH$_2$O—C(=O)—CH=CH$_2$]$_2$ | —N[CH$_2$—CH$_2$O—C(=O)—CH=CH$_2$]$_2$ | —N[CH$_2$—CH$_2$O—C(=O)—CH=CH$_2$]$_2$ |
| —N[CH$_2$—CH$_2$—NH—C(=O)—CH=CH$_2$]$_2$ | —N[CH$_2$—CH$_2$—NH—C(=O)—CH=CH$_2$]$_2$ | —N[CH$_2$—CH$_2$—NH—C(=O)—CH=CH$_2$]$_2$ |

| R$_7$ | R$_8$ | R$_9$ |
|---|---|---|
| —OH, | —OH, | —OH, |
| —NH$_2$, | —NH$_2$, | —NH$_2$, |
| —N(CH$_2$—CH$_2$—OH)$_2$, | —N(CH$_2$—CH$_2$—OH)$_2$, | —N(CH$_2$—CH$_2$—OH)$_2$, |
| —N(CH$_2$—CH$_2$—NH$_2$)$_2$, | —N(CH$_2$—CH$_2$—NH$_2$)$_2$, | —N(CH$_2$—CH$_2$—NH$_2$)$_2$, |
| —O—C(=O)—CH=CH$_2$, | —O—C(=O)—CH=CH$_2$, | —O—C(=O)—CH=CH$_2$, |
| —(CH$_2$—CH$_2$—O)$_w$H, | —(CH$_2$—CH$_2$—O)$_y$H, | —(CH$_2$—CH$_2$—O)$_z$H, |
| —(CH$_2$—CH$_2$—CH$_2$—O)$_w$H, | —(CH$_2$—CH$_2$—CH$_2$—O)$_y$H, | —(CH$_2$—CH$_2$—CH$_2$—O)$_z$H, |
| —N[CH$_2$O—C(=O)CH=CH$_2$]$_2$, | —N[CH$_2$O—C(=O)CH=CH$_2$]$_2$, | —N[CH$_2$O—C(=O)CH=CH$_2$]$_2$, |
| —N[CH$_2$—CH$_2$—O—C(=O)—CH=CH$_2$]$_2$, | —N[CH$_2$—CH$_2$—O—C(=O)—CH=CH$_2$]$_2$, | —N[CH$_2$—CH$_2$—O—C(=O)—CH=CH$_2$]$_2$, |
| or | or | or |
| —N[CH$_2$—CH$_2$—NH—C(=O)—CH=CH$_2$]$_2$, | —N[CH$_2$—CH$_2$—NH—C(=O)—CH=CH$_2$]$_2$, | —N[CH$_2$—CH$_2$—NH—C(=O)—CH=CH$_2$]$_2$, |
| NHC(=O)CH=CH2 | NHC(=O)CH=CH2 | NHC(=O)CH=CH2 |
| where | where | where |
| each w is, | each y is, | each z is, |
| independently, | independently, | independently, |
| an | an | an |
| integer | integer | integer |
| from 1 to | from 1 to | from 1 to |
| 18. | 18. | 18. |
| —N(CH$_2$—CH$_2$—OH)$_2$, | —N(CH$_2$—CH$_2$—OH)$_2$, | —N(CH$_2$—CH$_2$—OH)$_2$, |
| —N(CH$_2$—CH$_2$—NH$_2$)$_2$, | —N(CH$_2$—CH$_2$—NH$_2$)$_2$, | —N(CH$_2$—CH$_2$—NH$_2$)$_2$, |
| —O—C(=O)—CH=CH$_2$, | —O—C(=O)—CH=CH$_2$, | —O—C(=O)—CH=CH$_2$, |
| —N[CH$_2$O—C(=O)CH=CH$_2$]$_2$, | —N[CH$_2$O—C(=O)CH=CH$_2$]$_2$, | —N[CH$_2$O—C(=O)CH=CH$_2$]$_2$, |
| —N[CH$_2$—CH$_2$—O—C(=O)—CH=CH$_2$]$_2$, | —N[CH$_2$—CH$_2$—O—C(=O)—CH=CH$_2$]$_2$, | —N[CH$_2$—CH$_2$—O—C(=O)—CH=CH$_2$]$_2$, |
| or | or | or |
| —N[CH$_2$—CH$_2$—NH—C(=O)—CH=CH$_2$]$_2$. | —N[CH$_2$—CH$_2$—NH—C(=O)—CH=CH$_2$]$_2$. | —N[CH$_2$—CH$_2$—NH—C(=O)—CH=CH$_2$]$_2$. |
| —N(CH$_2$—CH$_2$—OH)$_2$, | —N(CH$_2$—CH$_2$—OH)$_2$, | —N(CH$_2$—CH$_2$—OH)$_2$, |
| —N(CH$_2$—CH$_2$—NH$_2$)$_2$, | —N(CH$_2$—CH$_2$—NH$_2$)$_2$, | —N(CH$_2$—CH$_2$—NH$_2$)$_2$, |
| —N[CH$_2$O—C(=O)CH=CH$_2$]$_2$, | —N[CH$_2$O—C(=O)CH=CH$_2$]$_2$, | —N[CH$_2$O—C(=O)CH=CH$_2$]$_2$, |
| or | or | or |
| —O—C(=O)—CH=CH$_2$. | —O—C(=O)—CH=CH$_2$. | —O—C(=O)—CH=CH$_2$. |
| —N(CH$_2$—CH$_2$—OH)$_2$ | —N(CH$_2$—CH$_2$—OH)$_2$ | —N(CH$_2$—CH$_2$—OH)$_2$ |
| —OH | —OH | —OH |
| —NH$_2$ | —NH$_2$ | —NH$_2$ |
| —N(CH$_2$—CH$_2$—OH)$_2$ | —N(CH$_2$—CH$_2$—OH)$_2$ | —N(CH$_2$—CH$_2$—OH)$_2$ |
| —N(CH$_2$—CH$_2$—NH$_2$)$_2$ | —N(CH$_2$—CH$_2$—NH$_2$)$_2$ | —N(CH$_2$—CH$_2$—NH$_2$)$_2$ |
| —O—C(=O)—CH=CH$_2$ | —O—C(=O)—CH=CH$_2$ | —O—C(=O)—CH=CH$_2$ |
| —N[CH$_2$O—C(=O)CH=CH$_2$]$_2$, | —N[CH$_2$O—C(=O)CH=CH$_2$]$_2$, | —N[CH$_2$O—C(=O)CH=CH$_2$]$_2$, |
| —N[CH$_2$—CH$_2$O—C(=O)—CH=CH$_2$]$_2$ | —N[CH$_2$—CH$_2$O—C(=O)—CH=CH$_2$]$_2$ | —N[CH$_2$—CH$_2$O—C(=O)—CH=CH$_2$]$_2$ |
| —N[CH$_2$—CH$_2$—NH—C(=O)—CH=CH$_2$]$_2$ | —N[CH$_2$—CH$_2$—NH—C(=O)—CH=CH$_2$]$_2$ | —N[CH$_2$—CH$_2$—NH—C(=O)—CH=CH$_2$]$_2$ |

Non-limiting examples of compounds represented by formula IV include, but are not limited to, the following compounds:

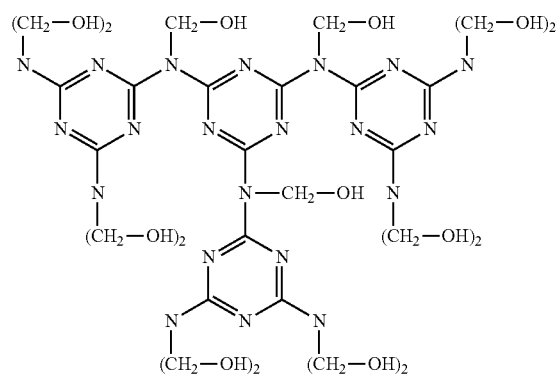

27

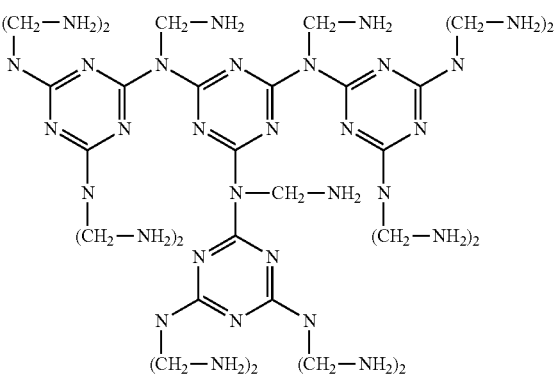

28

29
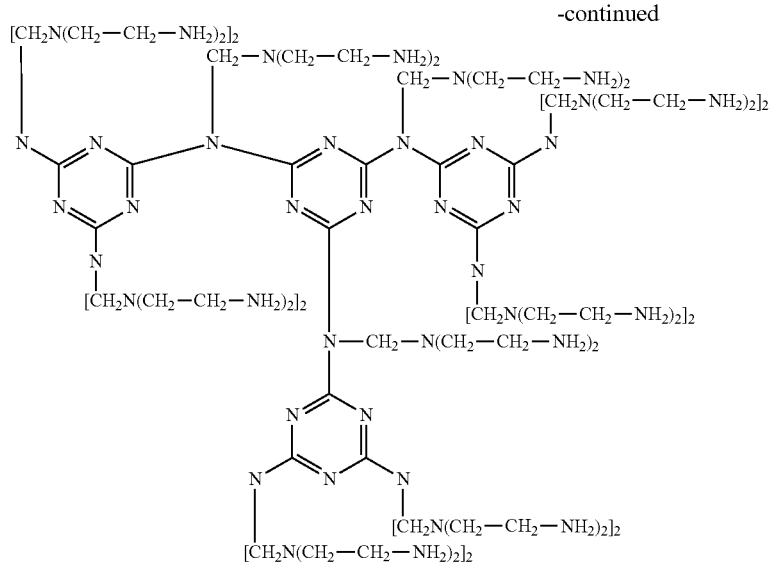
30
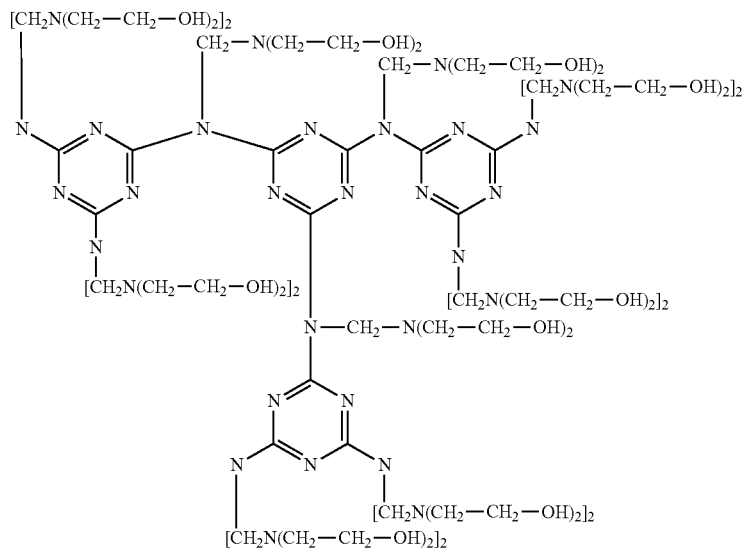
31
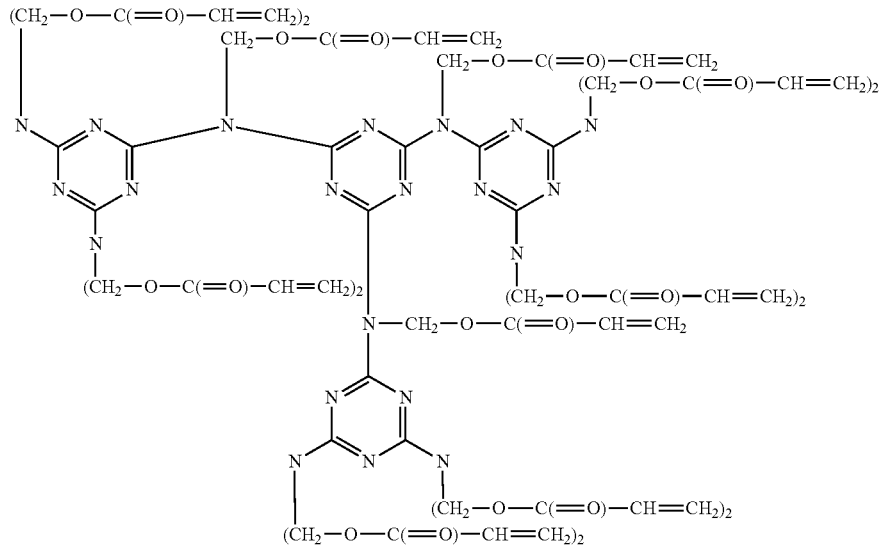

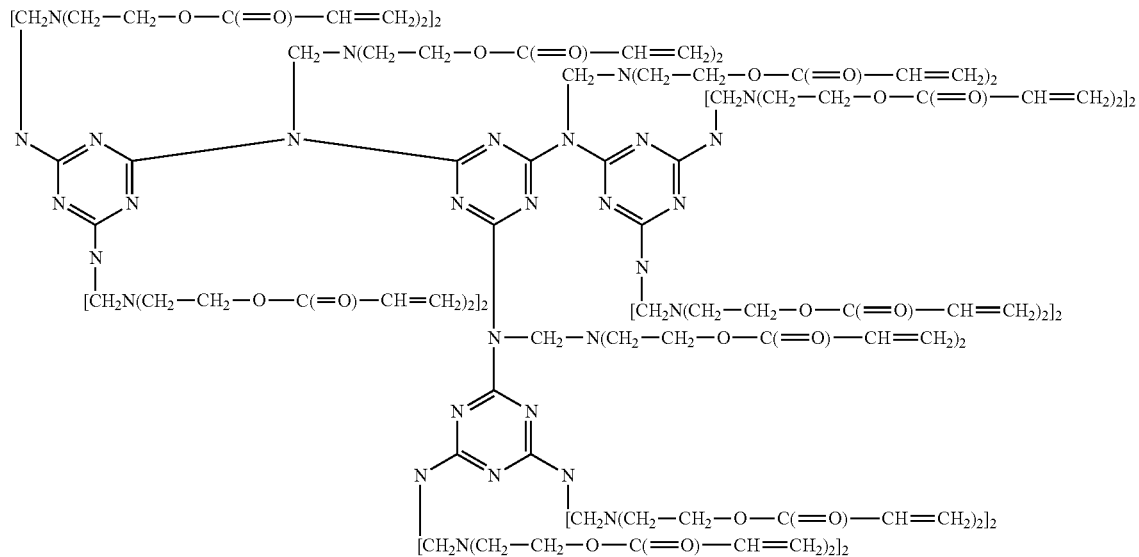

32

In some embodiments, a method for preparing compounds described herein may comprise: (a) contacting a phenolic compound or a melamine compound with formaldehyde to form a hydroxymethyl compound; and (b) contacting the hydroxymethyl compound with an acrylic compound to form the compounds described herein.

In some embodiments, contacting the phenolic compound or the melamine compound with the formaldehyde may be performed in the presence of a basic catalyst. Specific examples of the basic catalyst include, but are not limited to, alkali earth metal hydroxide, alkali metal carbonic acid salt and alkali metal hydroxide. Examples of phenolic compounds that may be used include, but are not limited to, phenol, bisphenol A, bisphenol F, bisphenol S, bisphenol sulphone, bisphenol sulphoxide, bisphenol chloral, bisphenolvinylidene dichloride, and bisphenol methylenedifluoride. Examples of melamine compounds that may be used include, but are not limited to, melamine and melamine cyanurate. The phenolic compound or melamine compound and the formaldehyde may be contacted in a molar ratio from about 1:3 to about 1:5, from about 1:3 to about 1:4.5, or from about 1:3 to about 1:4. Specific examples include, but are not limited to, about 1:5, about 1:4, about 1:3.5, about 1:3, and ranges between any two of these values (including their endpoints). The contacting of the phenolic compound or the melamine compound with the formaldehyde in the presence of the basic catalyst may be performed by mixing the phenolic compound or the melamine compound with the formaldehyde and the basic catalyst in a solution. During the contacting of the phenolic compound or the melamine compound and the formaldehyde, the pH of the solution may be maintained from about pH 8 to about pH 11, from about pH 8 to about pH 10.5, from about pH 8 to about pH 10, from about pH 8 to about pH 9, or from about pH 8 to about pH 8.5. Specific examples include, but are not limited to, about pH 8, about pH 8.5, about pH 9, about pH 9.5, about pH 10, about pH 11, and ranges between any two of these values (including their endpoints).

During the contacting of the phenolic compound or the melamine compound and the formaldehyde, the phenolic compound or the melamine compound, the formaldehyde and the basic catalyst may be heated to a temperature from about 50° C. to about 90° C., from about 50° C. to about 75° C., from about 50° C. to about 70° C., or from about 50° C. to about 60° C. Specific examples also include, but are not limited to, about 50° C., about 65° C., about 70° C., about 80° C., about 85° C., about 90° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Specific examples include, but are not limited to, about 2 hours, about 3 hours, about 4 hours, about 5 hours, about 6 hours, and ranges between (and including the endpoints of) any two of these values.

The contacting between the phenolic compound or the melamine compound and the formaldehyde may result in the formation of hydroxymethyl compounds such as, for example, mono, di, tri, tetra, penta, or hexa hydroxymethyl derivatives. These hydroxymethyl derivatives may be obtained by varying the stoichiometric ratios of the reactants and the reaction conditions. Non-limiting examples of hydroxymethyl compounds include trihydroxymethyl phenol, tetrahydroxymethyl bisphenol A, tetrahydroxymethyl bisphenol F, tetrahydroxymethyl bisphenol S, tetrahydroxymethyl bisphenol sulphone, tetrahydroxymethyl bisphenol sulphoxide, tetrahydroxymethyl bisphenol chloral, tetrahydroxymethyl bisphenolvinylidene dichloride, tetrahydroxymethyl bisphenol methylenedifluoride, hexahydroxymethyl melamine and pentadecahydroxymethyl melamine cyanurate.

In some embodiments, contacting the hydroxymethyl compound with the acrylic compound may comprise contacting the hydroxymethyl compound with the acrylic compound in a molar ratio from about 1:4 to about 1:8, from about 1:4 about 1:7, from about 1:4 to about 1:6, or from about 1:4 to about 1:5. Specific examples include, but are not limited to, about 1:4, about 1:5, about 1:6.5, about 1:7, about 1:8 and ranges between any two of these values. The acrylic compound may be acrylic anhydride, acryloyl chloride, acrylic acid, or combinations thereof. In some embodiments, the contacting step may be carried out in the presence or absence of an antioxidant, such as tert-butylhydro-quinone, substituted quinones, butylated hydroxyl toluene, or any combination thereof.

In some embodiments, the reaction of hydroxymethyl compound and the acrylic compound may be brought to about completion by heating the reaction mixture to a temperature from about 25° C. to about 90° C., from about 25° C. to about 75° C., from about 25° C. to about 70° C., from about 25° C. to about 60° C., or from about 25° C. to about 40° C. Specific examples also include, but are not limited to, about 25° C., about 50° C., about 65° C., about 70° C., about 80° C., about 85° C., about 90° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Specific examples include, but are not limited to, about 2 hours, about 3 hours, about 4 hours, about 5 hours, about 6 hours, and ranges between (and including the endpoints of) any two of these values.

The compounds with acrylate functional groups of the current disclosure may be cured to form resins. Curing may be performed by mixing the acrylate compounds with peroxide, azo, diazo, per acids, or per esters with catalysts such as benzoylperoxide and cobalt octanoate, or other transition metal co-catalysts. The mixture may be allowed to cure at room temperature for several hours to overnight.

In some embodiments, compounds of the current disclosure may be reacted with one or more suitable monounsaturated monocarboxylic acids, such as, for example, acrylic acid, methacrylic acid, cyanoacrylic acid, crotonic acid, α-phenylacrylic acid, methoxyacrylic acid, monomethyl ester of maleic acid, monomethyl ester of fumaric acid, and the like, and mixtures thereof. After such reactions, the compounds may be cured as described herein.

The polymers obtained by the methods described herein may be used as, for example, binders in paints and coatings. In addition, various additives, such as pigments, coalescing agents, rheology modifiers, fungicides, plasticizers, nitrates, and the like, may be added to the coatings. These paints with multi-functional acrylate binders may display high glass transition temperatures, and may be resistant to abrasion, and easily cure at room temperature. The coatings may generally be applied to any substrate. The substrate may be, for example, an article, an object, a vehicle or a structure. Although no particular limitation is imposed on the substrate to be used in the present disclosure, exemplary substrates include, but are not limited to, building exteriors, vehicles, bridges, airplanes, metal railings, fences, glasses, plastics, metals, ceramics, wood, stones, cement, fabric, paper, leather, and combinations or laminations thereof may be used. The coating may be applied to a substrate by, for example, spraying, dipping, rolling, brushing, or any combination thereof.

The resins formed from the acrylate compounds described herein may be used for production of composites, either alone or as interpenetrating polymer networks (IPNs) with other thermosets, such as epoxy and unsaturated polyesters. Further, these resins may also find use in, for example, hydrogels, polyacrylate super absorbent polymers (SAPs), adhesives, composites, sealants, fillers, fire retardants, crosslinking agents, and the like. In addition, resins may be prepared with different functionality such that a different number of acrylate functional groups per monomer are exhibited. For example, by using a resol precursor a resin with 4 acrylate groups per monomer may be prepared. In contrast, a melamine precursor may result in 6 acrylate groups per monomer. Such resins with tailored functionality may be used to improve the physical, mechanical and/or chemical properties, and curing characteristics of acrylate emulsions. The resins described herein may work as a crosslinking agent for commercial acrylate resins, and/or as a wetting polymeric surfactant, and such properties may find applications in super absorbent polymers for soil treatment.

The compounds of the present disclosure may also be used as a precursor for developing new and improved products for hydrophobic soil treatment, or for use in water and sewage treatment facilities with compounds that act as water-clarification agents. Further, compounds described herein may find use in carbon fibers, crosslinking agents for SAPs, adhesives, lamination, photo printing, room-temperature curing applications, photo curing, and the like.

EXAMPLES

Example 1

Preparation of Compound 1

About 100 grams of phenol and 270 grams of formalin solution (37% concentration) were mixed in a five-neck reaction flask fitted with a condenser, mechanical stirrer, dropping funnel, and a thermometer. The reaction was started by adding 100 mL of 40% sodium hydroxide solution drop wise, and the pH of the reaction mixture was adjusted to pH 10. The reaction mixture was heated to about 65° C. for 2 hours with efficient mechanical mixing, and the pH was maintained at between pH 9-pH 10. At the end of this period, the reaction mixture was cooled and neutralized with a cold (5-10° C.) solution of sodium dihydrogen phosphate. An oily viscous layer was separated from the reaction mixture, dissolved in ethanol, desalted, and dried with molecular sieves. The product was evaporated by rotary evaporators and dried under vacuum to obtain a resol compound.

About 18.2 grams (0.1 mole) of the above obtained resol was added slowly to 86 grams (0.4 mole) of acrylic acid anhydride (analar grade) and 0.1 gram of tert-butylhydroquinone in a reaction vessel with efficient mechanical mixing. The reaction vessel was immersed in water bath at 60° C., and the resol solution in ethylacetate was slowly added from the dropping funnel with mixing for one hour. The reaction was continued at about 60° C. for two hours, and at the end of this period the temperature was raised to about 80° C. for one hour. The excess of unreacted acrylic anhydride and acrylic acid by-products were distilled under vacuum. A viscous acrylated resol (compound 1) was obtained. The product was characterized and its curing properties were investigated by differential scanning calorimetry (DSC).

Similar product was prepared by reaction of resol with acryloyl chloride in the presence of triethylamine as a solvent and HCl, at ambient temperature (25° C.).

Example 2

Preparation of Compound 9

About 100 grams of bisphenol F and 270 grams of formalin solution (37% concentration) were mixed in a five-neck reaction flask fitted with a condenser, mechanical stirrer, dropping funnel, and a thermometer. The reaction was started by adding 100 mL of 40% sodium hydroxide solution drop wise, and the pH of the reaction mixture was adjusted to pH 10. The reaction mixture was heated to about 65° C. for 2 hours, and the pH was maintained between pH 9 and pH 10. At the end of this period, the reaction mixture was cooled and neutralized with cold (5-10° C.) solution of sodium dihydrogen phosphate. An oily viscous layer was separated from the reaction mixture, dissolved in ethanol, desalted, and dried with molecular sieves. The product was evaporated by rotary evaporators and dried under vacuum to obtain the tetrahydroxymethyl bisphenol compound. The number of hydroxymethyl groups in the resin was determined by Moisture Evolution Analysis (MEA) and DSC (Perkin Elmer).

About 32 grams (0.1 mole) of the above obtained bisphenol compound was mixed with 86 grams (0.4 mole) of acrylic acid anhydride (analar grade) and 0.1 gram of tert-butylhydroquinone in a reaction vessel. The reaction mixture was heated to about 60° C. and the tetrahydroxymethyl bisphenol solution in THF was slowly added from the dropping funnel with mixing for one hour. The reaction was continued at about 60° C. for two hours, and at the end of this period the temperature was raised to about 80° C. for one hour. The excess of unreacted acrylic anhydride and acrylic acid by-products were distilled under vacuum, and a viscous acrylated bisphenol compound (compound 9) was obtained. The product was characterized and evaluated by DSC. The above product can also be prepared by substituting acrylic acid with acryloyl chloride and carrying out the reaction in the presence of triethylamine as a solvent and HCl, at ambient temperature (25° C.).

Similar procedure was followed to prepare bisphenol A derivatives (compound 19).

Example 3

Preparation of Hexahydroxymethyl Melamine (Compound 20)

About 126 grams of melamine and 650 grams of formalin solution (37% concentration) were mixed in a five-neck reaction flask fitted with a condenser, mechanical stirrer, dropping funnel, and a thermometer. The reaction was started by adding 10% sodium carbonate solution drop wise, and the pH of the reaction mixture was adjusted to between pH 8.5 and pH 9. The reaction mixture was heated to about 65-70° C. for 3 hours, with mixing. At the end of this period, the reaction mixture became transparent indicating the conversion of melamine to its hydroxymethyl derivative. The product was cooled to room temperature, and the excess of unreacted formaldehyde was removed. The product was purified to obtain compound 20.

Similar methods may be followed to prepare melamine cyanurate derivatives (compound 27).

Example 4

Preparation of Compound 21

About 30.6 grams of compound 20 was dissolved in 250 mL of methanol in a one liter auto-clave system from Analis s.a/n.v (Belgium) that is fitted with a mechanical stirrer, and which could be operated under controlled temperature and pressure. The system was secured and connected to an ammonia gas cylinder. The system was flushed with $N_2$, and mixed for 10 minutes to dissolve the compound Ammonia gas was fed to the autoclave until the pressure reached 1.5 atmospheres. The reaction temperature was maintained at about 50-60° C. using a cooling jacket of the autoclave for 2 hours. At the end of this period, the system was cooled to room temperature, and the system was flushed with $N_2$ gas to remove unreacted ammonia gas. The product was evaporated and dried under vacuum to obtain compound 21. The product was characterized and the number of amino groups was estimated from the CHN quantitative analysis data. The product was evaluated as curing agent for epoxy resins.

Similar methods may be followed to prepare melamine cyanurate derivatives (compound 28).

Example 5

Preparation of Compound 3

About 36.4 grams (0.2 mole) of resol (Example 1) is mixed with 200 mL of ethylacetate in a five-neck reaction flask fitted with a condenser, mechanical stirrer, dropping funnel, and a thermometer. The reaction mixture is heated to about 50° C. and about 30 grams (about 0.11 mole) of polyethyleneglycol monoglycidylether (PEGMGE, epoxy equivalent 135) is slowly added from the dropping funnel for 1 hour. The reaction is continued for two more hours and the mixture is cooled to ambient temperature. The excess of unreacted PEGMGE is removed by addition of 100 grams of water with vigorous mixing. The viscous oily product obtained is purified and dried under vacuum to obtain a resol with a PEG functional group.

About 18.2 grams (0.1 mole) of the above obtained PEG-resol is mixed with 86 grams (0.4 mole) of acrylic acid anhydride (analar grade) and 0.1 gram of tert-butylhydroquinone in a reaction vessel. The reaction mixture is heated to about 60° C. and the PEG-resol is slowly added from the dropping funnel with mixing for one hour. The reaction is continued at about 60° C. for two hours, and at the end of this period the temperature is raised to about 80° C. for one hour. The excess of unreacted acrylic anhydride and acrylic acid by-products are distilled under vacuum, and a viscous acrylated resol with PEG functional group (compound 3) is obtained. The product is evaluated as self emulsifying polyacrylate resins that are suitable for hydrophilic smart self cleaning paint.

Example 6

Preparation of Compound 10

About 33.6 grams of tetrahydroxymethyl bisphenol compound (Example 2) is mixed with 200 mL of ethanol in a five-neck reaction flask fitted with a condenser, mechanical stirrer, dropping funnel, and a thermometer. The reaction mixture is heated to about 50° C. and about 30 grams (about 0.11 mole) of polyethyleneglycol monoglycidylether (PEG-MGE, epoxy equivalent 135) is slowly added from the dropping funnel for 1 hour. The reaction is continued for two more hours and the mixture is cooled to ambient temperature. The excess of unreacted PEGMGE is removed by addition of 100 grams of water with vigorous mixing. The viscous oily product obtained is purified and dried under vacuum to obtain a tetrahydroxymethyl bisphenol compound with a PEG functional group.

About 18.2 grams (0.1 mole) of the above obtained PEG-bisphenol is mixed with 86 grams (0.4 mole) of acrylic acid anhydride (analar grade) and 0.1 gram of tert-butylhydroquinone in a reaction vessel. The reaction mixture is heated to about 60° C. and the PEG-bisphenol is slowly added from the dropping funnel with mixing for one hour. The reaction is continued at about 60° C. for two hours, and at the end of this period the temperature is raised to about 80° C. for one hour. The excess of unreacted acrylic anhydride and acrylic acid by-products are distilled under vacuum, and a viscous acrylated bisphenol with PEG functional group (compound 10) is obtained.

Similar procedures are followed to prepare bisphenol A derivatives (compound 16).

Example 7

Preparation of Compound 22

About 60 grams (0.6 mole) of diethanolamine was obtained in a three-neck reaction vessel fitted with condenser, magnetic stirrer, and a dropping funnel immersed in water bath at 60° C. About 33.6 grams of hexahydroxymethyl melamine compound of Example 3 diluted with 10 mL of ethanol was added drop wise with continuous mixing for one hour, and the reaction mixture was heated to about 80° C. The reaction was continued with efficient mixing for two more hours. At the end of the reaction, about 200 grams of cold water was added to dissolve the unreacted diethanolamine. The product obtained was re-dissolved in ethanol, dried with molecular sieves (4A), evaporated by a rotary evaporator, and dried under vacuum at about 60° C. and 0.1 mmHg for 6 hours to obtain compound 22. The amine derivatives were evaluated as curing agent for epoxy resins by DSC.

Similar methods may be followed to prepare melamine cyanurate derivatives (compound 30).

Example 8

Preparation of Compound 5

About 30.6 grams of PEG-resol of Example 5 is mixed with 250 mL of methanol in a one liter auto-clave system that is fitted with a mechanical stirrer, and which could be operated under controlled temperature and pressure. The system is secured and connected to an ammonia gas cylinder. The system is flushed with $N_2$, and mixed for 10 minutes to dissolve the compound Ammonia gas is fed to the autoclave until the pressure reached 1.5 atmospheres. The reaction temperature is maintained at about 50-60° C. using a cooling jacket of the autoclave for 2 hours. At the end of this period, the system is cooled to room temperature and the system is flushed with $N_2$ gas to remove unreacted ammonia gas. The product is evaporated and dried under vacuum to obtain a resol with PEG and amino groups.

About 18.2 grams (0.1 mole) of the above obtained amino-PEG-resol is dissolved in 2 moles triethylamine. About 36 grams (0.4 mole) of acryloyl chloride dissolved in methylene chloride is added drop wise with mixing and the reaction is carried out at 25° C. When the addition is complete, the temperature is raised to 30° C. and the reaction is continued for further one hour. Later, about 200 grams of water is added, and the viscous acrylamide with molecular surfactant group resin is separated and compound 5 is obtained. The compound is used as hydrogel for soil conditioning.

Similar methods are used to prepare compound 12 and using PEG-bisphenol as the precursor (Example 6).

Example 9

Preparation of Compound 26

About 26.4 grams (0.1 mole) of compound 21 dissolved in triethylamine is added slowly to 36 grams (0.4 mole) of acryloyl chloride in a reaction vessel immersed in water bath at 25° C. for one hour. The reaction mixture is then heated to about 30° C. and the reaction is continued for two hours. At the end of this period, the excess of unreacted acrylol chloride and acrylic acid by-products are extracted with water, and a viscous acrylated melamine compound (compound 26) is obtained.

Similar methods may be followed to prepare melamine cyanurate derivatives (compound 33).

Example 10

Curing of Acrylate Resins 10 grams of acrylate compound 1 prepared in Example 1 was mixed with 0.05 grams of benzoylperoxide and 0.02 grams of cobalt octanoate. The mixture was left to cure at ambient temperature for about 6 hours to about 12 hours. The cured polyacrylate resin had a glass transition temperature of 120-150° C. and a thermal decomposition temperature of 430° C. As will be appreciated, the acrylate resin can be easily cured at ambient temperature and that the acrylate resin displays high glass transition and thermal decomposition temperatures.

Example 11

Evaluation of Polymers for Surfactant Properties

The diethanolamine compound prepared in Example 7 was evaluated as follows. About 50 grams of water and 50 grams of vegetable oil were added to a separating funnel. The two liquids formed separate layers. About 0.5 grams of compound 22 was added to the separating funnel and mixed. A homogenous emulsion was obtained demonstrating the surfactant properties of the compound.

Example 12

Preparation of a Hydrogel

About 10 grams of compound 5 was mixed 2 grams of polyacrylate, 0.05 grams of benzoylperoxide and 0.02 grams of cobalt octanoate and left to cure at ambient temperature. The cured resin was later neutralized with potassium hydroxide. About 10 grams of the neutralized resin was immersed in distilled water. The product swelled in volume (about 200% increase in weight) due to absorption of water.

Example 13

Preparation of a Coating

A coating composition is prepared using the following components: 40 grams of chromium oxide pigment, 2 grams of thickener (hydroxyethyl cellulose), 150 grams of solvent (water), 70 grams of binder (cured compound 3), 0.3 grams of coalescing agent (2,2,4-trimethyl-1,3-pentanediol mono (2-methylpropanoate)), and 0.05 grams of bactericide. The components are mixed under high shear for 30 minutes to form the coating composition.

A cast iron rod is coated with the paint prepared above. A similar rod is also coated with a commercially available paint. The paint is allowed to dry and scribed with an X through the paint down to the metal. The rods are placed in a salt fog chamber (5% NaCl, 35° C.) for 200 hours. At the end of this period, the rods are visually inspected for corrosion and peeling of the paint at the site of damage. The rod sprayed with paint comprising compound 3 will display less corrosion and peeling of the paint, when compared to the rod sprayed with a commercial paint.

Example 14

Water Retention Properties of Hydrogel

The hydrogel prepared in Example 13 is mixed with soil and chickpea seeds are planted in a pot. A similar soil without hydrogel is used for planting in a second pot. The soil is wetted in both the pots during planting of the seeds. After initial watering, the seeds are allowed to germinate without addition of any water so as to replicate drought conditions. The pot with hydrogel-soil mixture will display shoots suggesting the water retaining properties of hydrogel in soil.

Example 15

Water Clarification Agent

A turbid water is prepared by mixing reagent grade chemicals ($CaCO_3$, $MgCO_3$), naturally occurring clays and humic acid in distilled water. About 500 mL of the turbid water is placed in a beaker and mixed stirrer paddle. The polymer of compound 24 is added to the water and mixed. The mixing is stopped and the sample is allowed to settle for about 15 minutes. A similar turbid water without compound 24 polymer is used for the test. A 30 mL sample of supernatant water is siphoned from a point 1 inch below the surface of the settled water. The turbidity of the sample is measured using a Hach Model 18900 ratio turbidity meter. The turbidity of the sample water with compound 24 polymer is lower than the water that is not treated with the polymer of compound 24.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURES, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and so on" is used, in general, such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and so on). In those instances where a convention analogous to "at least one of A, B, or C, and so on" is used, in general, such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and so on). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and so on. As a non-limiting example, each range discussed herein can be readily broken down into a lower third, middle third and upper third, and so on. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:
1. A compound of formula II:

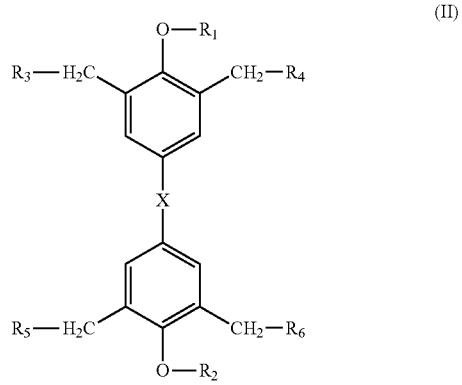

(II)

wherein:
$R_1$ is H, —($CH_2$—$CH_2$—O)$_n$H, —($CH_2$—$CH_2$—$CH_2$—O)$_n$H, or —($CH_2$—$CH_2$—O)$_n$—($CH_2$—$CH_2$—$CH_2$—O)$_n$H, wherein each n is, independently, an integer from 1 to 18;

$R_2$ is H, —C(=O)—CH=$CH_2$, —($CH_2$—$CH_2$—O)$_p$H, —($CH_2$—$CH_2$—$CH_2$—O)$_p$H, or —($CH_2$—$CH_2$—O)$_p$—($CH_2$—$CH_2$—$CH_2$—O)$_p$H, wherein each p is, independently, an integer from 1 to 18;

$R_3$ is —N($CH_2$—$CH_2$—$NH_2$)$_2$, —O—C(=O)—CH=$CH_2$, N[$CH_2$O—C(=O)—CH=$CH_2$]$_2$, —NHC(=O)CH=$CH_2$, —($CH_2$—$CH_2$—O)$_q$H, —($CH_2$—$CH_2$—$CH_2$—O)$_q$H, —N[$CH_2$—$CH_2$—O—C(=O)—CH=$CH_2$]$_2$, or —N[$CH_2$—$CH_2$—NH—C(=O)—CH=$CH_2$]$_2$, wherein each q is, independently, an integer from 1 to 18;

$R_4$ is —N($CH_2$—$CH_2$—$NH_2$)$_2$, —O—C(=O)—CH=$CH_2$, —NH—C(=O)CH=$CH_2$, —N[$CH_2$O—C(=O)—CH=$CH_2$]$_2$, —($CH_2$—$CH_2$—O)$_r$H, —($CH_2$—$CH_2$—$CH_2$—O)$_r$H, —N[$CH_2$—$CH_2$—O—C(=O)—CH=$CH_2$]$_2$, or —N[$CH_2$—$CH_2$—NH—C(=O)—CH=$CH_2$]$_2$, wherein each r is, independently, an integer from 1 to 18;

$R_5$ is —N($CH_2$—$CH_2$—$NH_2$)$_2$, —O—C(=O)—CH=$CH_2$, —N[$CH_2$O—C(=O)—CH=$CH_2$]$_2$, —NH—C(=O)CH=$CH_2$, —($CH_2$—$CH_1$—O)$_s$H, —($CH_2$—$CH_2$—$CH_2$—O)$_s$H, —N[$CH_2$—$CH_2$—O—C(=O)—CH=$CH_2$]$_2$, or —N[$CH_2$—$CH_2$—NH—C(=O)—CH=$CH_2$]$_2$, wherein each s is, independently, an integer from 1 to 18;

$R_6$ is —N($CH_2$—$CH_2$—$NH_2$)$_2$, —O—C(=O)—CH=$CH_2$, —N[$CH_2$O—C(=O)—CH=$CH_2$]$_2$, —NH—C(=O)CH=$CH_2$, —($CH_2$—$CH_2$—O)$_t$H, —($CH_2$—$CH_2$—$CH_2$—O)$_t$H, —N[$CH_2$—$CH_2$—O—C(=O)—CH=$CH_2$]$_2$, or —N[$CH_2$—$CH_2$—NH—C(=O)—CH=$CH_2$]$_2$, wherein each t is, independently, an integer from 1 to 18; and X is —$CH_2$—, —C($CH_3$)$_2$—, —S—, —S(=O)$_2$—, —S(=O)—, —CH(CCl$_3$)—, —C(Cl)$_2$—, —O—, or —C(F)$_2$—.

2. The compound of claim 1, wherein X is —C($CH_3$)$_2$—, $R_1$ is —($CH_2$—$CH_2$—O)$_n$H, $R_2$ is —($CH_2$—$CH_2$—O)$_p$H, $R_3$ is —O—C(=O)—CH=$CH_2$, $R_4$ is —O—C(=O)—CH=$CH_2$, $R_5$ is —O—C(=O)—CH=$CH_2$, and $R_6$ is —O—C(=O)—CH=$CH_2$.

3. The compound of claim 1, wherein X is —C($CH_3$)$_2$—, $R_1$ is —($CH_2$—$CH_2$—O)$_n$H, $R_2$ is —($CH_2$—$CH_2$—O)$_p$H, $R_3$ is —N($CH_2$—$CH_2$—$NH_2$)$_2$, $R_4$ is —N($CH_2$—$CH_2$—$NH_2$)$_2$, $R_5$ is —N($CH_2$—$CH_2$—$NH_2$)$_2$, and $R_6$ is —N($CH_2$—$CH_2$—$NH_2$)$_2$.

4. The compound of claim 1, wherein X is —C($CH_3$)$_2$—, $R_1$ is —($CH_2$—$CH_2$—O)$_n$H, $R_2$ is —($CH_2$—$CH_2$—O)$_p$H, $R_3$ is —N[$CH_2$O—C(=O)—CH=$CH_2$]$_2$, $R_4$ is —N[$CH_2$O—C(=O)—CH=$CH_2$]$_2$, $R_5$ is —N[$CH_2$O—C(=O)—CH=$CH_2$]$_2$, and $R_6$ is —N[$CH_2$O—C(=O)—CH=$CH_2$]$_2$.

5. The compound of claim 1, wherein X is —C($CH_3$)$_2$—, $R_1$ is H, $R_2$ is H, $R_3$ is —O—C(=O)—CH=$CH_2$, $R_4$ is —O—C(=O)—CH=$CH_2$, $R_5$ is —O—C(=O)—CH=$CH_2$, and $R_6$ is —O—C(=O)—CH=$CH_2$.

6. The compound of claim 1, wherein X is —$CH_2$—, $R_1$ is —($CH_2$—$CH_2$—O)$_n$H, $R_2$ is —($CH_2$—$CH_2$—O)$_p$H, $R_3$ is —O—C(=O)—CH=$CH_2$, $R_4$ is —O—C(=O)—CH=$CH_2$, $R_5$ is —O—C(=O)—CH=$CH_2$, and $R_6$ is —O—C(=O)—CH=$CH_2$.

7. The compound of claim 1, wherein X is —$CH_2$—, $R_1$ is —($CH_2$—$CH_2$—O)$_n$H, $R_2$ is —($CH_2$—$CH_2$—O)$_p$H, $R_3$ is —N(CH$_2$—CH$_2$—NH$_2$)$_2$, R$_4$ is —N(CH$_2$—CH$_2$—NH$_2$)$_2$, R$_5$ is —N(CH$_2$—CH$_2$—NH$_2$)$_2$, and R$_6$ is —N(CH$_2$—CH$_2$—NH$_2$)$_2$.

8. The compound of claim 1, wherein X is —CH$_2$—, R$_1$ is —(CH$_2$—CH$_2$—O)$_n$H, R$_2$ is —(CH$_2$—CH$_2$—O)$_p$H, R$_3$ is —N[CH$_2$O—C(=O)—CH=CH$_2$]$_2$, R$_4$ is —N[CH$_2$O—C(=O)—CH=CH$_2$]$_2$, R$_5$ is —N[CH$_2$O—C(=O)—CH=CH$_2$]$_2$, and R$_6$ is —N[CH$_2$O—C(=O)—CH=CH$_2$]$_2$.

9. The compound of claim 1, wherein X is —CH$_2$—, R$_1$ is H, R$_2$ is H, R$_3$ is —O—C(=O)—CH=CH$_2$, R$_4$ is —O—C(=O)—CH=CH$_2$, R$_5$ is —O—C(=O)—CH=CH$_2$, and R$_6$ is —O—C(=O)—CH=CH$_2$.

10. The compound of claim 1, wherein the compound is incorporated into a polymer, a coating composition, or a hydrogel.

* * * * *

UNITED STATES PATENT AND TRADEMARK OFFICE
CERTIFICATE OF CORRECTION

| | | |
|---|---|---|
| PATENT NO. | : 9,834,522 B2 | Page 1 of 2 |
| APPLICATION NO. | : 14/768217 | |
| DATED | : December 5, 2017 | |
| INVENTOR(S) | : Adam | |

It is certified that error appears in the above-identified patent and that said Letters Patent is hereby corrected as shown below:

In Column 1, Line 9, delete "Application Ser. No." and insert -- Application No. --, therefor.

In Column 5, Line 33, delete "–(CH$_2$–CH$_2$–O)–" and insert -- –(CH$_2$–CH$_2$–O)$_n$– --, therefor.

In Column 5, Line 38, delete "–(CH$_2$–CH$_2$–O)–" and insert -- –(CH$_2$–CH$_2$–O)$_n$– --, therefor.

In Column 15, in Table 3, below "R$_3$", Line 9, delete "–NH–C(=O–CH=CH2" and insert -- –NH–C(=O)–CH=CH$_2$ --, therefor.

In Column 16, in Table 3, below "R$_4$", Line 9, delete "–NH–C(=O–CH=CH$_2$" and insert -- –NH–C(=O)–CH=CH$_2$ --, therefor.

In Column 17, in Table 3, under "R$_5$", Line 1, delete "–NH–C(=O–CH=CH$_2$" and insert -- –NH–C(=O)–CH=CH$_2$ --, therefor.

In Column 18, in Table 3, under "R$_6$", Line 1, delete "–NH–C(=O–CH=CH$_2$" and insert -- –NH–C(=O)–CH=CH$_2$ --, therefor.

In Column 26, in Table 6, below "R$_2$", Line 14, delete "where n" and insert -- where p --, therefor.

In Column 55, in Table 12, under "R$_1$", Line 15, delete "–N[CH$_2$O–C(=0)CH=CH$_2$]$_2$," and insert -- –N[CH$_2$O–C(=O)CH=CH$_2$]$_2$, --, therefor.

In Column 55, in Table 12, under "R$_2$", Line 15, delete "–N[CH$_2$O–C(=0)CH=CH$_2$]$_2$," and insert -- –N[CH$_2$O–C(=O)CH=CH$_2$]$_2$, --, therefor.

In Column 55, in Table 12, below "R$_4$", Line 23, delete "–N[CH$_2$O–C(=0)CH=CH$_2$]$_2$," and insert -- –N[CH$_2$O–C(=O)CH=CH$_2$]$_2$, --, therefor.

Signed and Sealed this
Nineteenth Day of June, 2018

Andrei Iancu
*Director of the United States Patent and Trademark Office*

CERTIFICATE OF CORRECTION (continued)
U.S. Pat. No. 9,834,522 B2

In Column 55, in Table 12, below "$R_5$", Line 23, delete "–N[CH$_2$O–C(=0)CH=CH$_2$]$_2$," and insert -- –N[CH$_2$O–C(=O)CH=CH$_2$]$_2$, --, therefor.

In Column 56, in Table 12, under "$R_3$", Line 16, delete "–N[CH$_2$O–C(=0)CH=CH$_2$]$_2$," and insert -- –N[CH$_2$O–C(=O)CH=CH$_2$]$_2$, --, therefor.

In Column 56, in Table 12, below "$R_6$", Line 23, delete "–N[CH$_2$O–C(=0)CH=CH$_2$]$_2$," and insert -- –N[CH$_2$O–C(=O)CH=CH$_2$]$_2$, --, therefor.

In Column 57, in Table 12, below "$R_7$", Line 23, delete "–N[CH$_2$O–C(=0)CH=CH$_2$]$_2$," and insert -- –N[CH$_2$O–C(=O)CH=CH$_2$]$_2$, --, therefor.

In Column 57, in Table 12, below "$R_8$", Line 23, delete "–N[CH$_2$O–C(=0)CH=CH$_2$]$_2$," and insert -- –N[CH$_2$O–C(=O)CH=CH$_2$]$_2$, --, therefor.

In Column 58, in Table 12, below "$R_9$", Line 23, delete "–N[CH$_2$O–C(=0)CH=CH$_2$]$_2$," and insert -- –N[CH$_2$O–C(=O)CH=CH$_2$]$_2$, --, therefor.

In Column 65, Line 60, delete "compound Ammonia" and insert -- compound. Ammonia --, therefor.

In Column 67, Line 39, delete "compound Ammonia" and insert -- compound. Ammonia --, therefor.

In Column 72, Lines 10-11, in Claim 1, delete "–O–(=O)–CH=CH2," and insert -- –O–C(=O)–CH=CH2, --, therefor.

In Column 72, Line 26, in Claim 1, delete "(CH2–CH1–O)sH," and insert -- (CH2–CH2–O)sH, --, therefor.